United States Patent
Gouze

(10) Patent No.: US 11,814,654 B2
(45) Date of Patent: Nov. 14, 2023

(54) SOLUBLE FIBROBLAST GROWTH FACTOR RECEPTOR 3 (FGR3) POLYPEPTIDE FOR USE IN THE PREVENTION OR TREATMENT OF SKELETAL GROWTH RETARDATION DISORDERS

(71) Applicants: Institut National de la Sante et de la Recherche Medicale, Paris (FR); Université Paul Sabatier Toulouse III, Toulouse (FR)

(72) Inventor: Elvire Gouze, Vallauris (FR)

(73) Assignees: Institut National de la Sante et de la Recherche Medicale, Paris (FR); Université Paul Sabatier Toulouse III, Toulouse (FR)

( * ) Notice: Subject to any disclaimer, the term of this patent is extended or adjusted under 35 U.S.C. 154(b) by 353 days.

(21) Appl. No.: 16/906,046

(22) Filed: Jun. 19, 2020

(65) Prior Publication Data
US 2021/0032608 A1    Feb. 4, 2021

Related U.S. Application Data

(63) Continuation of application No. 14/759,535, filed as application No. PCT/EP2014/050800 on Jan. 16, 2014, now Pat. No. 10,724,014.

(51) Int. Cl.
| | |
|---|---|
| *A61K 38/17* | (2006.01) |
| *C07K 14/71* | (2006.01) |
| *A61P 19/00* | (2006.01) |
| *C12N 9/12* | (2006.01) |
| *A61K 38/00* | (2006.01) |

(52) U.S. Cl.
CPC .............. *C12N 9/12* (2013.01); *A61K 38/179* (2013.01); *A61P 19/00* (2018.01); *C07K 14/71* (2013.01); *A61K 38/00* (2013.01); *C12Y 207/10001* (2013.01)

(58) Field of Classification Search
CPC ... A61K 38/179; A61K 38/1709; C07K 14/71
See application file for complete search history.

(56) References Cited

U.S. PATENT DOCUMENTS

| | | | |
|---|---|---|---|
| 5,015,573 A | 5/1991 | Yarranton et al. | |
| 6,743,425 B2 | 6/2004 | Nakao | |
| 7,276,481 B2 | 10/2007 | Golembo et al. | |
| 7,498,416 B2 | 3/2009 | Yayon et al. | |
| 7,598,027 B2 | 10/2009 | Fernandez-Salas et al. | |
| 7,678,890 B2 | 3/2010 | Bosch et al. | |
| 7,982,014 B2 | 7/2011 | Williams et al. | |
| 8,043,618 B2 | 10/2011 | Sun et al. | |
| 8,101,721 B2 | 1/2012 | Yayon et al. | |
| 8,187,601 B2 | 5/2012 | Wenq et al. | |
| 8,338,569 B2 | 12/2012 | Marshall et al. | |
| 8,404,240 B2 | 3/2013 | Sun | |
| 8,410,250 B2 | 4/2013 | Ashkenazi et al. | |
| 8,426,396 B2 | 4/2013 | Horton et al. | |
| 8,445,445 B2 | 5/2013 | Brennan et al. | |
| 8,481,038 B2 | 7/2013 | Keer | |
| 8,614,183 B2 | 12/2013 | Hardinq et al. | |
| 8,685,931 B2 | 4/2014 | Brennan et al. | |
| 8,710,189 B2 | 4/2014 | Ashkenazi et al. | |
| 8,828,385 B2 | 9/2014 | Yavon et al. | |
| 8,962,556 B2 | 2/2015 | Yayon et al. | |
| 9,273,137 B2 | 3/2016 | Fang et al. | |
| 10,294,289 B2 | 5/2019 | Gouze et al. | |
| 10,724,014 B2 | 7/2020 | Gouze et al. | |
| 11,021,528 B2 | 6/2021 | Gouze et al. | |
| 2002/0193309 A1 | 12/2002 | Yayon | |
| 2003/0068313 A1 | 4/2003 | Nakao | |
| 2003/0235589 A1 | 12/2003 | Demopulos et al. | |
| 2004/0109850 A1 | 6/2004 | Jaiswal et al. | |
| 2005/0147612 A1 | 7/2005 | Yavon et al. | |
| 2008/0044419 A1* | 2/2008 | Yayon ..................... | A61P 17/06 424/139.1 |
| 2008/0171689 A1 | 7/2008 | Williams et al. | |
| 2009/0192133 A1 | 7/2009 | Horton et al. | |
| 2009/0202547 A1 | 8/2009 | Yayon et al. | |
| 2010/0003258 A1 | 1/2010 | Weng et al. | |
| 2010/0047251 A1 | 2/2010 | Yayon et al. | |
| 2010/0087627 A1 | 4/2010 | Marshall et al. | |

(Continued)

FOREIGN PATENT DOCUMENTS

| | | | |
|---|---|---|---|
| CN | 102219860 A | 10/2011 | |
| CN | 105121464 A | 12/2015 | |

(Continued)

OTHER PUBLICATIONS

Johnsson et al., Rheumatology(Oxford), 2009, vol. 48(11):1398-1401 (Abstract).*
Moon et al., Annals of the Rheumatic Diseases, 2015, vol. 74 (suppl. 2):217.*
Terada et al., Mol. Cell Biol. Res. Commun., 2001, vol. 4(6):365-373.*
Aviezer et al., Curr. Drug Targets, 2003, vol. 495):353-365.*
Extended European Search Report dated Dec. 20, 2022 for Application No. 22167483.1.
[No Author Listed], GenBank Accession No. JV574764.1. TSA: Macaca mulatta Mamu_241725 mRNA sequence. https://www.ncbi.nlm.nih.gov/nuccore/JV574764.1. Nov. 4, 2014. 2 pages.

(Continued)

*Primary Examiner* — Xiaozhen Xie
(74) *Attorney, Agent, or Firm* — Wolf, Greenfield & Sacks, P.C.

(57) ABSTRACT

The present invention relates to the prevention or treatment of skeletal growth retardation disorders, in particular skeletal diseases developed by patients that display abnormal increased activation of the fibroblast growth factor receptor 3 (FGFR3), in particular by expression of a prolonged activated mutant of FGFR3. More particularly, the present invention relates to a soluble FGFR3 for use in the prevention or treatment of achondroplasia.

11 Claims, 4 Drawing Sheets

Figure 1:
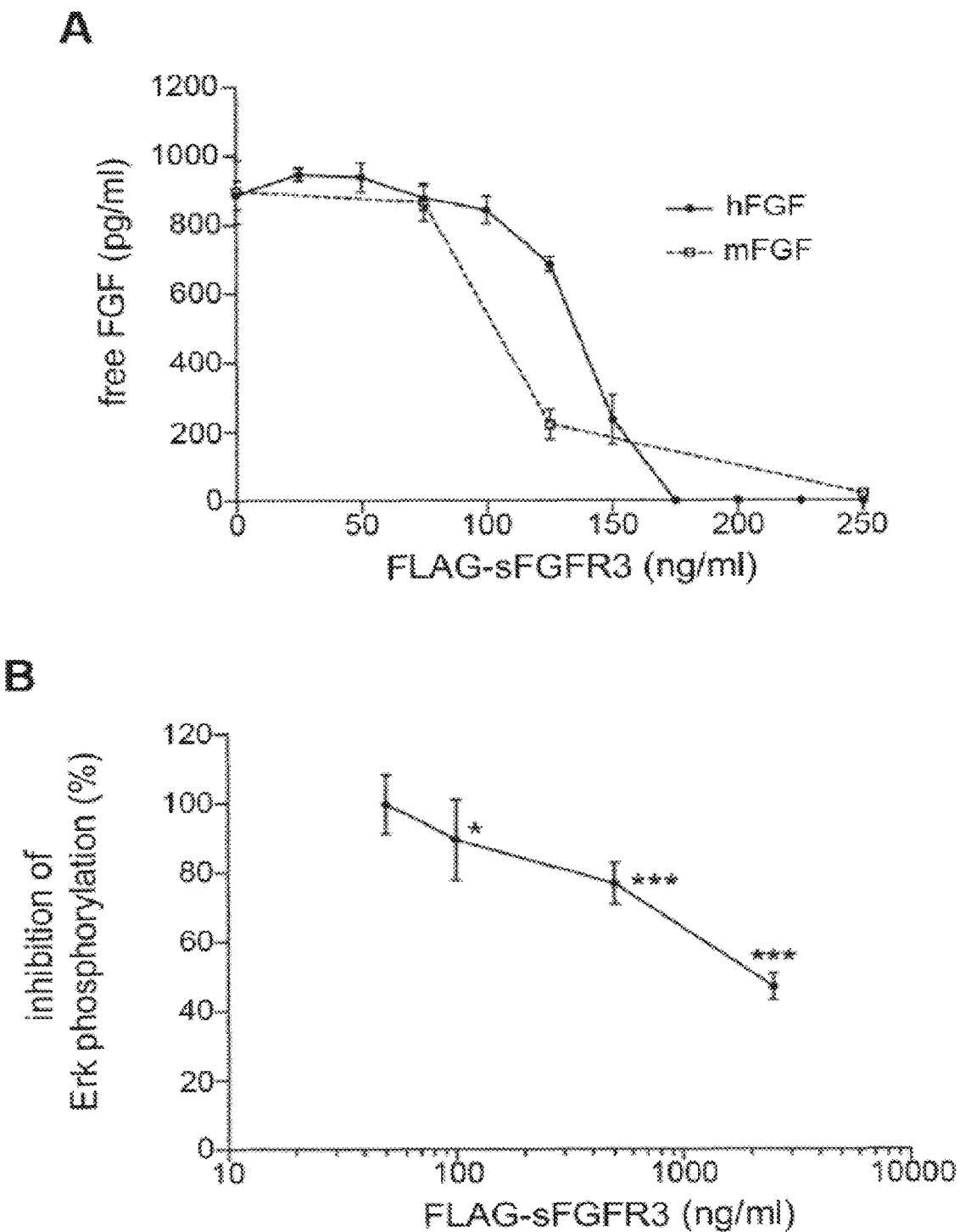

Specification includes a Sequence Listing.

(56) References Cited

U.S. PATENT DOCUMENTS

| | | |
|---|---|---|
| 2010/0158911 A1 | 6/2010 | Williams et al. |
| 2010/0291114 A1 | 11/2010 | Wiesmann |
| 2011/0053841 A1 | 3/2011 | Yayon et al. |
| 2012/0009200 A1 | 1/2012 | Sun et al. |
| 2012/0183541 A1 | 7/2012 | Brennan et al. |
| 2012/0219563 A1 | 8/2012 | Sun |
| 2012/0321606 A1 | 12/2012 | Wiesmann |
| 2012/0328599 A1 | 12/2012 | Bae et al. |
| 2013/0004492 A1 | 1/2013 | Marshall et al. |
| 2013/0046078 A1 | 2/2013 | Ashkenazi et al. |
| 2013/0058928 A1 | 3/2013 | Brennan et al. |
| 2013/0287776 A1 | 10/2013 | Ashkenazi et al. |
| 2014/0030259 A1 | 1/2014 | French |
| 2014/0187754 A1 | 7/2014 | Ashkenazi et al. |
| 2014/0274898 A1 | 9/2014 | Brennan et al. |
| 2014/0348817 A1 | 11/2014 | Jiang et al. |
| 2015/0344855 A1 | 12/2015 | Gouze |
| 2015/0353624 A1 | 12/2015 | Gouze |
| 2018/0148494 A1 | 5/2018 | Gouze et al. |
| 2018/0230197 A1 | 8/2018 | Gouze et al. |
| 2020/0190162 A1 | 6/2020 | Gouze et al. |
| 2020/0297799 A1 | 9/2020 | Gouze et al. |
| 2021/0009657 A1 | 1/2021 | Gouze et al. |
| 2021/0032607 A1 | 2/2021 | Gouze |
| 2021/0309718 A1 | 10/2021 | Gouze et al. |

FOREIGN PATENT DOCUMENTS

| | | |
|---|---|---|
| EA | 018700 B1 | 10/2013 |
| EP | 2083081 A1 | 7/2009 |
| EP | 1423428 B1 | 8/2009 |
| EP | 1910542 B1 | 12/2009 |
| EP | 1423428 B2 | 11/2012 |
| EP | 2679600 A1 | 1/2014 |
| JP | H11-507828 A | 7/1999 |
| JP | H11508358 A | 7/1999 |
| JP | 2003-104908 A | 4/2003 |
| JP | 2005-500034 A | 1/2005 |
| JP | 2007-526770 A | 9/2007 |
| JP | 2008-222711 A | 9/2008 |
| JP | 2011-529705 A | 12/2011 |
| JP | 2014-519308 A | 8/2014 |
| JP | 2016-506912 A | 3/2016 |
| RU | 2568066 C2 | 11/2015 |
| RU | 2751483 C2 | 7/2021 |
| WO | WO 96/41523 A1 | 12/1996 |
| WO | WO 02/102972 A2 | 12/2002 |
| WO | WO 02/102973 A2 | 12/2002 |
| WO | WO 2004/110487 A1 | 12/2004 |
| WO | WO 2005/082096 A2 | 9/2005 |
| WO | WO 2007/014123 A2 | 2/2007 |
| WO | WO 2007/144893 A2 | 12/2007 |
| WO | WO 2008/065543 A2 | 6/2008 |
| WO | WO 2008/133873 A2 | 11/2008 |
| WO | WO 2010/002862 A2 | 1/2010 |
| WO | WO 2010/017198 A2 | 2/2010 |
| WO | WO 2010/048026 A2 | 4/2010 |
| WO | WO 2010/111367 A1 | 9/2010 |
| WO | WO 2011/034940 A1 | 3/2011 |
| WO | WO 2011/084711 A2 | 7/2011 |
| WO | WO 2011/088196 A2 | 7/2011 |
| WO | WO 2012/088608 A1 | 7/2012 |
| WO | WO 2013/087744 A1 | 6/2013 |
| WO | WO 2014/018673 A2 | 1/2014 |
| WO | WO 2014/018841 A1 | 1/2014 |
| WO | WO 2014/071419 A2 | 5/2014 |
| WO | WO 2014/111467 A1 | 7/2014 |
| WO | WO 2014/111744 A1 | 7/2014 |
| WO | WO 2015/112886 A2 | 7/2015 |
| WO | WO 2016/110786 A1 | 7/2016 |
| WO | WO 2018/007597 A1 | 1/2018 |
| WO | WO 2019/057820 A1 | 3/2019 |

OTHER PUBLICATIONS

Babat et al., Spinal surgery in patients with Parkinson's disease: construct failure and progressive deformity. Spine (Phila Pa 1976). Sep. 15, 2004;29(18):2006-12. doi: 10.1097/01.brs.0000138306.02425.21.

Bhattacharya et al., Impact of genetic variation on three dimensional structure and function of proteins. PLoS One. Mar. 15, 2017;12(3):e0171355. doi: 10.1371/journal.pone.0171355. eCollection 2017.

Bose et al., Stress and obesity: the role of the hypothalamic-pituitary-adrenal axis in metabolic disease. Curr Opin Endocrinol Diabetes Obes. Oct. 2009;16(5):340-6. doi: 10.1097/MED.0b013e32832fa137.

Chellaiah et al., Mapping ligand binding domains in chimeric fibroblast growth factor receptor molecules. Multiple regions determine ligand binding specificity. J Biol Chem. Dec. 3, 1999;274(49):34785-94. doi: 10.1074/jbc.274.49.34785.

Chen et al., The extracellular domain of fibroblast growth factor receptor 3 inhibits ligand-independent dimerization. Sci Signal. Nov. 30, 2010;3(150):ra86. doi: 10.1126/scisignal.2001195.

Fenton et al., Rheostat positions: A new classification of protein positions relevant to pharmacogenomics. Med Chem Res. Jul. 2020;29(7):1133-1146. doi: 10.1007/s00044-020-02582-9. Epub Jun. 7, 2020.

Guo et al., Protein tolerance to random amino acid change. Proc Natl Acad Sci U S A. Jun. 22, 2004;101(25):9205-10. doi: 10.1073/pnas.0403255101. Epub Jun. 14, 2004.

Huang et al., A molecular mechanism for the generation of ligand-dependent differential outputs by the epidermal growth factor receptor. Elife. Nov. 30, 2021;10:e73218. doi: 10.7554/eLife.73218.

Hunter et al., Standard weight for height curves in achondroplasia. Am J Med Genet. Mar. 29, 1996;62(3):255-61. doi: 10.1002/(SICI)1096-8628(19960329)62:3<255::AID-AJMG10>3.0.CO;2-J.

Johnsson et al., Hand deformities are important signs of disease severity in patients with early rheumatoid arthritis. Rheumatology (Oxford). Nov. 2009;48(11):1398-401. doi: 10.1093/rheumatology/kep253. Epub Aug. 31, 2009.

Matsui et al., Genotype phenotype correlation in achondroplasia and hypochondroplasia. J Bone Joint Surg Br. Nov. 1998;80(6):1052-6. doi: 10.1302/0301-620x.80b6.9277.

Owen et al., Resting metabolic rate and body composition of achondroplastic dwarfs.Medicine (Baltimore). Jan. 1990;69(1):56-67. doi: 10.1097/00005792-199001000-00005.

Ramaswami et al., Treatment of achondroplasia with growth hormone: six years of experience. Pediatr Res. Oct. 1999;46(4):435-9. doi: 10.1203/00006450-199910000-00012.

Saint-Laurent et al., Early postnatal soluble FGFR3 therapy prevents the atypical development of obesity in achondroplasia. PLoS One. Apr. 13, 2018;13(4):e0195876. doi: 10.1371/journal.pone.0195876. eCollection 2018.

Van Buick et al., Novel Approaches for the Treatment of Alzheimer's and Parkinson's Disease. Int. J Mol Sci. 2019; 20(3): 719. https://doi.org/10.3390/ijms20030719.

Zhang et al., Research progress on the FGFR3 gene mutation and achondroplasia. Chinese Journal of Birth Health & Heredity. Dec. 2010; 18(5): 1-3.

Zimin et al., A new rhesus macaque assembly and annotation for next-generation sequencing analyses. Biol Direct. Oct. 14, 2014;9(1):20. doi: 10.1186/1745-6150-9-20.

International Search Report dated Aug. 7, 2013, for International Application No. PCT/IB2013/001480.

International Preliminary Report and Written Opinion dated Jul. 21, 2015, for International Application No. PCT/IB2013/001480.

Extended European Search Report dated Oct. 8, 2020, for Application No. EP 20167861.2.

International Search Report dated Mar. 7, 2014, for International Application No. PCT/EP2014/050800.

International Preliminary Report and Written Opinion dated Jul. 21, 2015, for International Application No. PCT/EP2014/050800.

International Search Report and Written Opinion dated Sep. 6, 2016, for International Application No. PCT/IB2016/000403.

International Preliminary Report on Patentability dated Jul. 20, 2017, for International Application No. PCT/IB2016/000403.

(56) References Cited

OTHER PUBLICATIONS

International Search Report and Written Opinion dated Sep. 25, 2017, for International Application No. PCT/EP2017/067119.
International Preliminary Report on Patentability dated Jan. 17, 2019, for International Application No. PCT/EP2017/067119.
International Search Report and Written Opinion dated Dec. 14, 2018, for International Application No. PCT/EP2018/075471.
International Preliminary Report on Patentability dated Apr. 2, 2020, for International Application No. PCT/EP2018/075471.
[No Author Listed], GenBank Accession No. NP_000133.1, downloaded from www.ncbi.nlm.nih.gov/protein/4503711. Sep. 21, 2020. 4.
[No Author Listed], GenBank Accession No. NP_075254.1, downloaded from: www.ncbi.nlm.nih.gov/protein/NP_075254.1. Jun. 19, 2020. 3 pages.
[No Author Listed], GenBank Accession No. P22607, downloaded from: https://www.ncbi.nlm.nih.gov/protein/P22607 on Apr. 5, 2018. 25 pages.
[No Author Listed], Japan Forum of Fetal Skeletal Dysplasia Wiki, 5. Fetal skeletal dysplasia. Accessible at: plaza.umin.ac.jp/-fskel/egi-bin/wiki/wiki.cgi?page=%C2%DB%BB%F9%B9%FC%B7%CF%C5%FD%BC%CO%B4%B5%B3%C6%CF%C0. Aug. 8, 2011. 8 pages.
Altaf et al., Ascorbate-enhanced chondrogenesis of ATDC5 cells. Eur Cell Mater. Nov. 9, 2006;12:64-9; discussion 69-70.
Auclair et al., Signal peptidase I: cleaving the way to mature proteins. Protein Sci. Jan. 2012;21(1):13-25. doi: 10.1002/pro.757. Epub Nov. 22, 2011.
Aviezer et al., Fibroblast growth factor receptor-3 as a therapeutic target for Achondroplasia—Genetic short limbed dwarfism. Curr Drug Targets. 2003;4(5):353-65.
Bellus et al., Achondroplasia is defined by recurrent G380R mutations of FGFR3. Am J Hum Genet. 1995;56(2):368-73.
Bertola et al., Hepatocyte growth factor induces glucose uptake in 3T3-L1 adipocytes through a Gab1/phosphatidylinositol 3-kinase/Glut4 pathway. J Biol Chem. Apr. 6, 2007;282(14):10325-32. Epub Feb. 6, 2007.
Cassagnaud et al., Biotherapy for achondroplasia. European Society of Gene and Cell Therapy French Society of Cell and Gene Therapy Collaborative Congress. Oct. 29, 2012;A76-A77, Abstract P043.
Chen et al., Interaction of cartilage oligomeric matrix protein/thrombospondin 5 with aggrecan. J Biol Chem. Aug. 24, 2007;282(34):24591-8. Epub Jun. 22, 2007.
Chusho et al., Dwarfism and early death in mice lacking C-type natriuretic peptide. Proc Natl Acad Sci USA. 2001;98(7):4016-21.
Davidson et al., Fibroblast growth factor (FGF) 18 signals through FGF receptor 3 to promote chondrogenesis. J Biol Chem. 2005;280(21):20509-15.
Deng et al., Fibroblast growth factor receptor 3 is a negative regulator of bone growth. Cell. 1996;84(6):911-21.
Garcia et al., Postnatal soluble FGFR3 therapy rescues achondroplasia symptoms and restores bone growth in mice. Sci Transl Med. 2013;5(203):203ra124(1-11).
Garofalo et al., Skeletal dysplasia and defective chondrocyte differentiation by targeted overexpression of fibroblast growth factor 9 in transgenic mice. J Bone Miner Res. 1999; 14(11):1909-15.
Ghivtzzani, Gene therapy for achondroplasia. Accessible at: www.asgct.org/members/asgct_news/summer10/index.php?pagecontent=page2.html. Retrieved on Dec. 20, 2013 (1 page).
Harada et al., Sustained phosphorylation of mutated FGFR3 is a crucial feature of genetic dwarfism and induces apoptosis in the ATDC5 chondrogenic cell line via PLCgamma-activated STAT1. Bone. Aug. 2007;41(2):273-81. Epub Feb. 9, 2007.
He et al., FGFR3 heterodimerization in achondroplasia, the most common form of human dwarfism. J Biol Chem. 2011;286(15):13272-81.
He et al., Physical basis behind achondroplasia, the most common form of human dwarfism. J Biol Chem. 2010;285(39):30103-14.
Horton et al., Achondroplasia. Lancet. 2007;370(9582):162-72.
Horton et al., Fibroblast growth factor receptor 3 mutations in achondroplasia and related forms of dwarfism. Rev Endocr Metab Disord. Dec. 2002;3(4):381-5.
Hunt et al., Bioactivity and metabolism of C-type natriuretic peptide in normal man. J Clin Endocrinol Metab. Jun. 1994;78(6):1428-35.
Hwang et al., High-level expression and purification of a designed angiopoietin-1 chimeric protein, COMP-Ang1, produced in Chinese hamster ovary cells. Protein J. Aug. 2008;27(5):319-26. doi: 10.1007/s10930-008-9140-5.
Jang, Identification and characterization of soluble isoform of fibroblast growth factor receptor 3 in human SaOS-2 osteosarcoma cells. Biochem Biophys Res Commun. 2002;292(2):378-82.
Jin et al., A novel FGFR3-binding peptide inhibits FGFR3 signaling and reverses the lethal phenotype of mice mimicking human thanatophoric dysplasia. Hum Mol Genet. 2012;21(26):5443-55.
Johnston et al., Fibroblast Growth Factor Receptors (FGFRs) Localize in Different Cellular Compartments. J Biol Chem. 1995;270(51):30643-50.
Krejci et al., NF449 is a novel inhibitor of fibroblast growth factor receptor 3 (FGFR3) signaling active in chondrocytes and multiple myeloma cells. J Biol Chem. 2010;285(27):20644-53.
Laederich et al., FGFR3 targeting strategies for achondroplasia. Expert Rev Mol Med. 2012;14:e11(1-17). Published Jan. 19, 2012. doi:10.1017/erm.2012.4.
Laws et al., Progression of kyphosis in mdx mice. J Appl Physiol (1985). Nov. 2004;97(5):1970-7. Epub Jul. 2, 2004.
Li et al., A novel decoy receptor fusion protein for FGF-2 potently inhibits tumour growth. Br J Cancer. Jul. 8, 2014;111(1):68-77. doi: 10.1038/bjc.2014.282. Epub May 29, 2014.
Lodish et al., Section 17.4: Translocation of Secretory Proteins across the ER Membrane. Molecular Cell Biology, Fourth Edition. W.H. Freeman and Company (2000) (5 pages).
Lorget et al., Evaluation of the therapeutic potential of a CNP analog in a Fgfr3 mouse model recapitulating achondroplasia. Am J Hum Genet. 2012;91(6):1108-14.
Louboutin et al., Strategies for CNS-directed gene delivery: in vivo gene transfer to the brain using SV40-derived vectors. Gene Ther. Jun. 2007;14(12):939-49. Epub Apr. 19, 2007.
Martinez-Frias et al., Review of the recently defined molecular mechanisms underlying thanatophoric dysplasia and their potential therapeutic implications for achondroplasia. Am J Med Genet A. 2010;152A(1):245-55. doi:10.1002/ajmg.a.33188.
Ming et al., The research progress in FGFR3 mutations and achondroplasia. Chinese Journal of Birth Health & Heredity. 2010;18(5):1-2; 13.
Monsonego-Ornan et al., FGF receptors ubiquitylation: dependence on tyrosine kinase activity and role in downregulation. FEBS Lett. 2002;528(1-3):83-9.
Monsonego-Ornan et al., The transmembrane mutation G380R in fibroblast growth factor receptor 3 uncouples ligand-mediated receptor activation from down-regulation. Mol Cell Biol. 2000;20(2):516-22.
Naski et al., Repression of hedgehog signaling and BMP4 expression in growth plate cartilage by fibroblast growth factor receptor 3. Development. 1998;125(24):4977-88.
Ornitz, FGF signaling in the developing endochondral skeleton. Cytokine Growth Factor Rev. 2005;16(2):205-213. doi:10.1016/j.cytogfr.2005.02.003. Author Manuscript. 15 pages.
Papakostas et al., Development of an efficiently cleaved, bioactive, highly pure FLAG-tagged recombinant human Mullerian Inhibiting Substance. Protein Expr Purif. Mar. 2010;70(1):32-8. doi: 10.1016/j.pep.2009.09.004. Epub Sep. 13, 2009.
Place et al., Aggrecan-mimetic, glycosaminoglycan-containing nanoparticles for growth factor stabilization and delivery. Biomacromolecules. 2014;15(2):680-9.
Placone et al., Direct assessment of the effect of the Gly380Arg achondroplasia mutation on FGFR3 dimerization using quantitative imaging FRET. PLoS One. 2012;7(10):e46678(1-7).
Reardon et al., Craniosynostosis associated with FGFR3 pro250arg mutation results in a range of clinical presentations including unisutural sporadic craniosynostosis. J Med Genet. 1997;34(8):632-6.

(56) References Cited

OTHER PUBLICATIONS

Richette et al., Achondroplasia: from genotype to phenotype. Joint Bone Spine. 2008;75(2):125-30.
Rodino-Klapac et al., Persistent expression of FLAG-tagged micro dystrophin in nonhuman primates following intramuscular and vascular delivery. Mol Ther. Jan. 2010;18(1):109-17. doi: 10.1038/mt.2009.254. Epub Nov. 10, 2009.
Rousseau et al., Mutations in the gene encoding fibroblast growth factor receptor-3 in achondroplasia. Nature. 1994;371(6494):252-4.
Rousseau et al., Mutations of the fibroblast growth factor receptor-3 gene in achondroplasia. Horm Res. 1996;45(1-2):108-10.
Roussel et al., A point mutation in the extracellular domain of the human CSF-1 receptor (c-fms proto-oncogene product) activates its transforming potential. Cell. Dec. 23, 1988;55(6):979-88. (Abstract only).
Salles et al., Translation studies in children. Arch Pediatr. 2009;16(6):664-6. (8 pages).
Shiang et al., Mutations in the transmembrane domain of FGFR3 cause the most common genetic form of dwarfism, achondroplasia. Cell. 1994;78(2):335-42.
Shirley et al., Achondroplasia: manifestations and treatment. J Am Acad Orthop Surg. Apr. 2009;17(4):231-41.
Sturla et al., FGFR3IIIS: a novel soluble FGFR3 spliced variant that modulates growth is frequently expressed in tumour cells. Br J Cancer. 2003;89(7):1276-84.
Su et al., Reduction of arthritis and pneumonitis in motheaten mice by soluble tumor necrosis factor receptor. Arthritis Rheum. 1998;41(1):139-49.
Terada et al., Fibroblast growth factor receptor 3 lacking the Ig IIIb and transmembrane domains secreted from human squamous cell carcinoma DJM-1 binds to FGFs. Mol Cell Biol Res Commun. 2001;4(6):365-73.
Terpe, Overview of tag protein fusions: from molecular and biochemical fundamentals to commercial systems. Appl Microbiol Biotechnol. Jan. 2003;60(5):523-33. Epub Nov. 7, 2002.
Tomlinson et al., Alternative splicing of fibroblast growth factor receptor 3 produces a secreted isoform that inhibits fibroblast growth factor-induced proliferation and is repressed in urothelial carcinoma cell lines. Cancer Res. 2005;65(22):10441-9.
Vajo et al., The molecular and genetic basis of fibroblast growth factor receptor 3 disorders: the achondroplasia family of skeletal dysplasias, Muenke craniosynostosis, and Crouzon syndrome with acanthosis niqricans. Endocr Rev. 2000;21(1):23-39.
Wang et al., Antitumor activity of a recombinant soluble ectodomain of mutant human fibroblast growth factor receptor-2 IIIc. Mol Cancer Ther. 2011;10(9):1656-66.
Webster et al., Constitutive activation of fibroblast growth factor receptor 3 by the transmembrane domain point mutation found in achondroplasia. EMBO J. 1996;15(3):520-7.
Wright et al., Clinical management of achondroplasia. Arch Dis Child. 2012;97(2):129-34.
Xie et al., Intermittent PTH (1-34) injection rescues the retarded skeletal development and postnatal lethality of mice mimicking human achondroplasia and thanatophoric dysplasia. Hum Mol Genet. 2012;21(18):3941-55.
Yasoda et al., Systemic administration of C-type natriuretic peptide as a novel therapeutic strategy for skeletal dysplasias. Endocrinology. 2009;150(7):3138-44.
Yu et al., Soluble vascular endothelial growth factor decoy receptor FP3 exerts potent antiangiogenic effects. Mol Ther. 2012;20(5):938-47.
Moon et al., THU0070 Dual Targeting of Kaempferol on the Kinase Activities of FGFR3 and RSK2 Suppresses Rheumatoid Arthritis in Vitro and in Vivo. Annals of the Rheumatic diseases. Jun. 2015; 74(Suppl 2): 217.
No Author Listed, Sequence and Isoforms P22607-1, P22607-2, P22607-3, P22607-4. Last updated Aug. 1991. 4 pages.
Pakula et al., Genetic analysis of protein stability and function. Annu Rev Genet. 1989;23:289-310. doi: 10.1146/annurev.ge.23.120189.001445.
Singer et al., Genes and Genomes—A Changing Perspective. University Science Books, Eds. vol. 1. 1998.

\* cited by examiner

A kyphotic index KI=[AB]/[CD]

| | Treatment | KI | % of animals with kyphosis (KI<4) |
|---|---|---|---|
| wt | PBS | 4,66 ± 0,72 | 0% |
| | 0.5ng sFGFR3 | 5,39 ± 0,55 | 0% |
| | 5ng sFGFR3 | 4,85 ± 0,64 | 0% |
| ach | PBS | 3,46 ± 0,65 * | 80% *** |
| | 0.5ng sFGFR3 | 4,34 ± 0,71 | 17% * |
| | 5ng sFGFR3 | 4,71 ± 0,68 | 6% |

B

| | Treatment | C7 | T11 | Lumbar compression§ |
|---|---|---|---|---|
| wt | All groups | 0% | 0% | 0% |
| ach | PBS | 88.9% | 70.1% | 58.6% |
| | 0.5ng sFGFR3 | 28.6% ## | 28.6% ## | 18.2% ## |
| | 5ng sFGFR3 | 40.0% ## | 0% ### | 16.6% ## |

SEQUENCE LISTING

<160> NUMBER OF SEQ ID NOS: 3

<210> SEQ ID NO 1
<211> LENGTH: 694
<212> TYPE: PRT
<213> ORGANISM: Artificial Sequence
<220> FEATURE:
<223> OTHER INFORMATION: Human soluble FGFR3 polypeptide (sFGFR3)

<400> SEQUENCE: 1

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Val Ser Leu Glu Ser Asn Ala Ser Met Ser
305                 310                 315                 320

Ser Asn Thr Pro Leu Val Arg Ile Ala Arg Leu Ser Ser Gly Glu Gly
                325                 330                 335

Pro Thr Leu Ala Asn Val Ser Glu Leu Glu Leu Pro Ala Asp Pro Lys
            340                 345                 350

Trp Glu Leu Ser Arg Ala Arg Leu Thr Leu Gly Lys Pro Leu Gly Glu
```

```
                    355                 360                 365
Gly Cys Phe Gly Gln Val Val Met Ala Glu Ala Ile Gly Ile Asp Lys
    370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                405                 410                 415

Met Lys Met Ile Gly Lys His Lys Asn Ile Ile Asn Leu Leu Gly Ala
            420                 425                 430

Cys Thr Gln Gly Gly Pro Leu Tyr Val Leu Val Glu Tyr Ala Ala Lys
        435                 440                 445

Gly Asn Leu Arg Glu Phe Leu Arg Ala Arg Arg Pro Pro Gly Leu Asp
    450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
        515                 520                 525

Asp Val His Asn Leu Asp Tyr Tyr Lys Lys Thr Thr Asn Gly Arg Leu
    530                 535                 540

Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690

<210> SEQ ID NO 2
<211> LENGTH: 2082
<212> TYPE: DNA
<213> ORGANISM: Artificial Sequence
<220> FEATURE:
<223> OTHER INFORMATION: Human soluble FGFR3 DNA sequence optimized to
      decrease GC content

<400> SEQUENCE: 2
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
```

-continued

```
ccagagcccg gccagcagga gcagttggtc ttcggcagcg gggatgctgt ggagctgagc      180
tgtcccccgc ccgggggtgg tcccatgggg cccactgtct gggtcaagga tggcacaggg      240
ctggtgccct cggagcgtgt cctggtgggg ccccagcggc tgcaggtgct gaatgcctcc      300
cacgaggact ccggggccta cagctgccgg cagcggctca cgcagcgcgt actgtgccac      360
ttcagtgtgc gggtgacaga cgctccatcc tcgggagatg acgaagacgg ggaggacgag      420
gctgaggaca caggtgtgga cacaggggcc cctactggac acggcccga gcggatggac       480 aagaagctgc tggccgtgcc ggccgccaac accgtccgct tccgctgccc agccgctggc      540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt tggcagcat ccggcagacg       720 tacacgctgg acgtgctgga cgctccccg caccggccca tcctgcaggc ggggctgccg       780
gccaaccaga cggcggtgct gggcagcgac gtggagttcc actgcaaggt gtacagtgac      840
gcacagcccc acatccagtg gctcaagcac gtggaggtga atggcagcaa ggtgggcccg      900
gacggcacac cctacgttac cgtgctcaag gtgtccctgg agtccaacgc gtccatgagc      960
tccaacacac cactggtgcg catcgcaagg ctgtcctcag ggagggccc acgctggcc      1020 aatgtctccg agctcgagct gcctgccgac cccaaatggg agctgtctcg ggcccggctg      1080
accctgggca agcccttgg ggagggctgc ttcggccagg tggtcatggc ggaggccatc      1140
ggcattgaca aggaccgggc cgccaagcct gtcaccgtag ccgtgaagat gctgaaagac      1200
gatgccactg acaaggacct gtcggacctg tgtctgaga tggagatgat gaagatgatc       1260
gggaaacaca aaaacatcat caacctgctg ggcgcctgca cgcagggcgg gcccctgtac      1320
gtgctggtgg agtacgcggc caagggtaac ctgcgggagt ttctgcgggc gcggcggccc      1380
ccgggcctgg actactcctt cgacacctgc aagccgccg aggagcagct caccttcaag       1440
gacctggtgt cctgtgccta ccaggtggcc cggggcatgg agtacttggc ctcccagaag      1500
tgcatccaca gggacctggc tgcccgcaat gtgctggtga ccgaggacaa cgtgatgaag      1560
atcgcagact cgggctggc ccgggacgtg cacaacctcg actactacaa gaagacaacc      1620
aacggccggc tgcccgtgaa gtggatggcg cctgaggcct tgtttgaccg agtctacact      1680
caccagagtg acgtctggtc ctttggggtc ctgctctggg agatcttcac gctgggggc      1740 tccccgtacc ccggcatccc tgtggaggag ctcttcaagc tgctgaagga gggccaccgc      1800
atggacaagc cgccaactg cacacacgac ctgtacatga tcatgcggga gtgctggcat      1860
gccgcgccct cccagaggcc caccttcaag cagctggtgg aggacctgga ccgtgtcctt      1920
accgtgacgt ccaccgacga gtacctggac ctgtcggcgc ctttcgagca gtactccccg      1980
ggtggccagg acaccccag ctccagctcc tcaggggacg actccgtgtt tgcccacgac      2040
ctgctgcccc ggccccacc cagcagtggg ggctcgcgga cg                          2082
```

<210> SEQ ID NO 3
<211> LENGTH: 806
<212> TYPE: PRT
<213> ORGANISM: Homo sapiens

<400> SEQUENCE: 3

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val

```
                20                  25                  30
Gly Arg Ala Ala Glu Val Pro Gly Pro Glu Pro Gly Gln Gln Glu Gln
                35                  40                  45

Leu Val Phe Gly Ser Gly Asp Ala Val Glu Leu Ser Cys Pro Pro Pro
 50                  55                  60

Gly Gly Gly Pro Met Gly Pro Thr Val Trp Lys Asp Gly Thr Gly
 65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
                115                 120                 125

Pro Ser Ser Gly Asp Asp Glu Asp Gly Glu Asp Glu Ala Glu Asp Thr
                130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
                195                 200                 205

Gln Gln Trp Ser Leu Val Met Glu Ser Val Val Pro Ser Asp Arg Gly
                210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
                290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Leu Pro Ala Glu Glu Leu Val Glu Ala Asp Glu
                355                 360                 365

Ala Gly Ser Val Tyr Ala Gly Ile Leu Ser Tyr Gly Val Gly Phe Phe
                370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
                435                 440                 445
```

```
Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
    595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
    675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
    755                 760                 765

Gln Tyr Ser Pro Gly Gln Asp Thr Pro Ser Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805
```

SOLUBLE FIBROBLAST GROWTH FACTOR RECEPTOR 3 (FGR3) POLYPEPTIDE FOR USE IN THE PREVENTION OR TREATMENT OF SKELETAL GROWTH RETARDATION DISORDERS

RELATED APPLICATIONS

This application is a continuation of U.S. application Ser. No. 14/759,535, (now U.S. Pat. No. 10,724,014), filed Jul. 7, 2015, which is a national stage filing under 35 U.S.C. § 371 of International Application No. PCT/EP2014/050800, filed Jan. 16, 2014, which claims priority to International Application No. PCT/IB2013/001480, filed Jan. 16, 2013, each of which are incorporated by reference herein in their entireties.

FIELD OF THE INVENTION

The present invention relates to the prevention or treatment of skeletal growth retardation disorders, in particular skeletal diseases and craniosynostosis, developed by patients that display abnormal increased activation of the fibroblast growth factor receptor 3 (FGFR3), in particular by expression of a constitutively activated mutant of FGFR3.

BACKGROUND OF THE INVENTION

Skeletal development in humans is regulated by numerous growth factors.

Among them Fibroblast Growth Factor Receptor 3 (FGFR3) has been described as a negative regulator of endochondral ossification. Mutations in the gene encoding for the FGFR3 have been shown to be responsible for the phenotype of numerous skeletal chondrodysplasias (1), including the thanatophoric dysplasias (TDI and TDII) (2) and achondroplasia (3), the most common form of short limb dwarfism. Children affected by achondroplasia suffer from deformations of the skull and vertebrae and abnormal long bone development, resulting in short stature and severe neurological and orthopedic complications (4, 5). Existing treatments are only designed to alleviate some of the complications, and are invasive and extreme (6, 7).

Achondroplasia is an autosomal dominant disorder caused by a point mutation in the gene for FGFR3 (Fgfr3ach) (8). In ~97% of affected patients, achondroplasia is caused by a G380R substitution in the transmembrane domain of the receptor (9, 10). This mutation in FGFR3 results in a gain of function (11), which prolongs activation of the tyrosine kinase activity of the receptor (12, 13). The G380R mutant FGFR3 remains ligand dependent for its dimerization and activation (12, 14); however, the presence of the mutation stabilizes the ligand/receptor complex (15) and slows down receptor internalization (12), thus extending subsequent intracellular Ras/MAPK pathway signaling (12). The resultant FGFR3 signaling is prolonged and steadily inhibits chondrocyte proliferation and differentiation in the growth plate (16). Cells expressing the mutant receptor do not mature and are not replaced by mineralized bone matrix, impairing lengthening of all bones formed by endochondral ossification (17, 18). These include the long bones of the appendicular skeleton, as well as the vertebrae, sternum, cranial base, and some bones in the skull where bone growth occurs at synchondroses, which are cartilaginous structures consisting of two opposed growth plates with a common zone of resting chondrocytes. As with endochondral growth plates in the long bones, synchondroses also become replaced by bone.

Despite an increased number of studies deciphering the mechanisms responsible for bone growth disturbances, there is still no cure available. Several therapeutic strategies are considered targeting mutant FGFR3 and its downstream signaling (16). Recently, Jin et al. have tested a novel peptide inhibiting FGFR3 signaling in a murine model of TDII (19). This study shows reversion of the neonatal lethality of TDII mice following in utero treatment and demonstrates the proof-of-concept that targeting FGFR3 in the extracellular compartment may be an effective strategy to treat FGFR3-related skeletal dysplasias.

Current therapies of achondroplasia include orthopedic surgeries such as leg lengthening and growth hormone therapy. However, leg lengthening inflicts a great pain on patients, and growth hormone therapy increases body height by means of periodic growth hormone injections starting from childhood. Further, growth ceases when injections are stopped. Consequently, it is desirable to develop a new achondroplasia therapy, as well as other skeletal growth retardation disorders including FGFR3-related skeletal diseases.

SUMMARY OF THE INVENTION

In a first aspect, the present invention relates to an isolated soluble Fibroblast Growth Factor Receptor 3 (sFGFR3) polypeptide or a functional equivalent thereof for use in the prevention or treatment of a skeletal growth retardation disorder.

In a second aspect, the present invention also relates to a pharmaceutical composition comprising an isolated sFGFR3 polypeptide or a functional equivalent thereof and a pharmaceutically acceptable carrier.

In a third aspect, the present invention further relates to a pharmaceutical composition for use in the prevention or treatment of a skeletal growth retardation disorder FGFR3-related skeletal disease comprising an isolated sFGFR3 polypeptide or a functional equivalent thereof and a pharmaceutically acceptable carrier.

In another aspect, the present invention relates to a method for preventing or treating a skeletal growth retardation disorder FGFR3-related skeletal disease comprising the step of administering a therapeutically effective amount of a sFGFR3 polypeptide or a pharmaceutical composition comprising such polypeptide to a subject in need thereof.

In still another aspect, the present invention further relates to an isolated sFGFR3 immunoadhesin as such as well as to its use as drug.

DETAILED DESCRIPTION OF THE INVENTION

The inventors have designed an effective therapeutic approach for achondroplasia by restoring bone growth. As shown herein, post-natal administration of recombinant soluble fibroblast growth factor receptor 3 (sFGFR3) acting as a decoy receptor to Fgfr3$^{ach/+}$ mice (a murine model of achondroplasia displaying a phenotype essentially identical to the human pathology, with shortening of all bones formed by endochondral ossification) results in normal skeletal growth preventing onset of achondroplasia symptoms and complications.

As disclosed herein, repeated subcutaneous injections of recombinant sFGFR3 throughout the growth period, normal skeletal growth can be restored in transgenic Fgfr3$^{ach/+}$ mice, resulting in normal body length and significant decrease in associated complications. Effective maturation of growth plate chondrocytes was restored in bones of treated mice, resulting in a dose-dependent enhancement of skeletal growth in Fgfr3$^{ach/+}$ mice. This resulted in normal stature associated with significant decrease in number and intensity of complications, without any evidence of toxicity. These results validate the use of soluble FGFR3 to restore bone growth and indicate its potential use as a promising therapy for achondroplasia and related skeletal disorders.

Therapeutic Methods and Uses

The present invention provides methods and compositions (such as pharmaceutical compositions) for preventing or treating a skeletal growth retardation disorder.

The present invention relates thus to an isolated soluble Fibroblast Growth Factor Receptor 3 (sFGFR3) polypeptide or a functional equivalent thereof for use in the prevention or treatment of a skeletal growth retardation disorder.

In one embodiment, the skeletal growth retardation disorder is an idiopathic skeletal growth retardation disorder.

In another embodiment, the skeletal growth retardation disorder is a FGFR3-related skeletal disease.

The terms "Fibroblast Growth Factor Receptor 3" ("FGFR3") or "FGFR3 receptor", as used herein, refer to any native or variant FGFR3 polypeptide. The FGFR3 gene, which is located on the distal short arm of chromosome 4, encodes a 806 amino acid protein precursor (fibroblast growth factor receptor 3 isoform 1 precursor). The FGFR3 receptor comprises an extracellular domain, a transmembrane domain and an intracellular domain. The naturally occurring human FGFR3 gene has a nucleotide sequence as shown in Genbank Accession number NM_000142.4 and the naturally occurring human FGFR3 protein has an aminoacid sequence as shown in Genbank Accession number NP_000133 and represented by SEQ ID NO: 3 below):

MGAPACALALCVAVAIVAGASSESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL

QAGLPANQTAVLGSDVEFHCKVYSDAQPHIQWLKHVEVNGSKVGPDGTPYV

TVLKTAGANTTDKELEVLSLHNVTFEDAGEYTCLAGNSIGFSHHSAWLVVL

PAEEELVEADEAGSVYAGILSYGVGFFFILVVAAVTLCRLRSPPKKGLGSP

TVHKISFPLKQVSLESNASMSSNTPLVRIARLSSGEGPTLANVSELELPAD

PKWELSRARLTLGKPLGEGCFGQVVMAEAIGIDKDRAAKPVTVAVKMLKDD

ATDKDLSDLVSEMEMMKMIGKHKNIINLLGACTQGGPLYVLVEYAAKGNLR

EFLRARRPPGLDYSFDTCKPPEEQLTFKDLVSCAYQVARGMEYLASQKCIH

RDLAARNVLVTEDNVMKIADFGLARDVHNLDYYKKTTNGRLPVKWMAPEAL

FDRVYTHQSDVWSFGVLLWEIFTLGGSPYPGIPVEELFKLLKEGHRMDKPA

NCTHDLYMIMRECWHAAPSQRPTFKQLVEDLDRVLTVTSDEYLDLSAPFEQ

YSPGGQDTPSSSSSGDDSVFAHDLLPPAPSSGGSRT

As used herein, the terms "extracellular domain of FGFR3" or "extracellular domain of FGFR3" refer to a polypeptide consisting of the amino acid sequence ranging from positions 1 to 375 of SEQ ID NO: 3 (sequence which is underlined above).

The term "polypeptide" means herein a polymer of amino acids having no specific length. Thus, peptides, oligopeptides and proteins are included in the definition of "polypeptide" and these terms are used interchangeably throughout the specification, as well as in the claims. The term "polypeptide" does not exclude post-translational modifications that include but are not limited to phosphorylation, acetylation, glycosylation and the like.

By an "isolated" polypeptide, it is intended that the polypeptide is not present within a living organism, e.g. within human body. However, the isolated polypeptide may be part of a composition or a kit. The isolated polypeptide is preferably purified.

As used herein, the term "soluble" refers to a polypeptide that is not bound to the cell membrane. Usually, a receptor is in soluble form when its amino acid sequence lacks the transmembrane domain. In this context, a form will be soluble if using conventional assays known to one of skill in the art most of this form can be detected in fractions that are not associated with the membrane, e.g., in cellular supernatants or serum.

A "native sequence" polypeptide refers to a polypeptide having the same amino acid sequence as a polypeptide derived from nature. Thus, a native sequence polypeptide can have the amino acid sequence of naturally-occurring polypeptide from any mammal (including human. Such native sequence polypeptide can be isolated from nature or can be produced by recombinant or synthetic means. The term "native sequence" polypeptide specifically encompasses naturally-occurring truncated or secreted forms of the polypeptide (e. g., an extracellular domain sequence), naturally-occurring variant forms (e. g., alternatively spliced forms) and naturally-occurring allelic variants of the polypeptide.

A polypeptide "variant" refers to a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the frame of the present application, the percentage of identity is calculated using a global alignment (i.e., the two sequences are compared over their entire length). Methods for comparing the identity and homology of two or more sequences are well known in the art. The "needle" program, which uses the Needleman-Wunch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Polypeptides consisting of an amino acid sequence "at least 80%, 85%, 90%, 95%, 96%, 97%, 98% or 99% identical" to a reference sequence may comprise mutations such as deletions, insertions and/or substitutions compared to the reference sequence. The polypeptide consisting of an amino acid sequence at least 80%, 85%, 90%, 95%, 96%, 97%, 98% or 99% identical to a reference sequence may correspond to an allelic variant of the reference sequence. It may for example only comprise substitutions compared to the reference sequence. The substitutions preferably correspond to conservative substitutions as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

A soluble FGFR3 polypeptide exerts an inhibitory effect on the biological activity of the FGFs proteins by binding to these proteins, thereby preventing them from binding to FGFR3 present on the surface of target cells. It is undesirable for a soluble FGFR3 polypeptide to become associated with the cell membrane.

In a preferred embodiment, the soluble FGFR3 polypeptide lacks any amino acid sequences corresponding to the transmembrane and/or intracellular domains from the FGFR3 polypeptide from which it is derived.

The terms "soluble FGFR3 polypeptide" or "sFGFR3", as used herein, refer to a polypeptide comprising or consisting of the extracellular region of the FGFR3 receptor, or a variant or a fragment thereof. For example, sFGFR3 may include all the extracellular domain of human FGFR3 except the second half of the third Ig-like domain (Ig IIIb) and the transmembrane domain of FGFR3 (i.e. a polypeptide comprising or consisting of a 694 amino acid sequence derived from the human FGFR3 receptor, as shown by SEQ ID NO: 1 below):

MGAPACALALCVAVAIVAGASSESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTGVVENKFGSIRQTYTLDVLERSPHRPIL

QAGLPANQTAVLGSDVEFHCKVYSDAQPHIQWLKHVEVNGSKVGPDGTPYV

TVLKVSLESNASMSSNTPLVRIARLSSGEGPTLANVSELELPADPKWELSR

ARLTLGKPLGEGCFGQVVMAEAIGIDKDRAAKPVTVAVKMLKDDATDKDLS

DLVSEMEMMKMIGKHKNIINLLGACTQGGPLYVLVEYAAKGNLREFLRARR

PPGLDYSFDTCKPPEEQLTFKDLVSCAYQVARGMEYLASQKCIHRDLAARN

VLVTEDNVMKIADFGLARDVHNLDYYKKTTNGRLPVKWMAPEALFDRVYTH

QSDVWSFGVLLWEIFTLGGSPYPGIPVEELFKLLKEGHRMDKPANCTHDLY

MIMRECWHAAPSQRPTFKQLVEDLDRVLTVTSTDEYLDLSAPFEQYSPGGQ

DTPSSSSSGDDSVFAHDLLPPAPPSSGGSRT

In one particular embodiment, the sFGFR3 polypeptide is encoded by a nucleic acid sequence defined by SEQ ID NO: 2 (below).

ATGGGCGCCCCTGCCTGCGCCCTCGCGCTCTGCGTGGCCGTGGCCATCGTG

GCCGGCGCCTCCTCGGAGTCCTTGGGGACGGAGCAGCGCGTCGTGGGGCGA

GCGGCAGAAGTCCCGGGCCCAGAGCCCGGCCAGCAGGAGCAGTTGGTCTTC

GGCAGCGGGGATGCTGTGGAGCTGAGCTGTCCCCCGCCCGGGGGTGGTCCC

ATGGGGCCCACTGTCTGGGTCAAGGATGGCACAGGGCTGGTGCCCTCGGAG

CGTGTCCTGGTGGGGCCCCAGCGGCTGCAGGTGCTGAATGCCTCCCACGAG

GACTCCGGGGCCTACAGCTGCCGGCAGCGGCTCACGCAGCGCGTACTGTGC

CACTTCAGTGTGCGGGTGACAGACGCTCCATCCTCGGGAGATGACGAAGAC

GGGGAGGACGAGGCTGAGGACACAGGTGTGGACACAGGGGCCCCTTACTGG

ACACGGCCCGAGCGGATGGACAAGAAGCTGCTGGCCGTGCCGGCCGCCAAC

ACCGTCCGCTTCCGCTGCCCAGCCGCTGGCAACCCCACTCCCTCCATCTCC

TGGCTGAAGAACGGCAGGGAGTTCCGCGGCGAGCACCGCATTGGAGGCATC

AAGCTGCGGCATCAGCAGTGGAGCCTGGTCATGGAAAGCGTGGTGCCCTCG

GACCGCGGCAACTACACCTGCGTCGTGGAGAACAAGTTTGGCAGCATCCGG

CAGACGTACACGCTGGACGTGCTGGAGCGCTCCCCGCACCGGCCCATCCTG

CAGGCGGGGCTGCCGGCCAACCAGACGGCGGTGCTGGGCAGCGACGTGGAG

TTCCACTGCAAGGTGTACAGTGACGCACAGCCCCACATCCAGTGGCTCAAG

CACGTGGAGGTGAATGGCAGCAAGGTGGGCCCGGACGGCACACCCTACGTT

ACCGTGCTCAAGGTGTCCCTGGAGTCCAACGCGTCCATGAGCTCCAACACA

CCACTGGTGCGCATCGCAAGGCTGTCCTCAGGGGAGGGCCCCACGCTGGCC

AATGTCTCCGAGCTCGAGCTGCCTGCCGACCCCAAATGGGAGCTGTCTCGG

GCCCGGCTGACCCTGGGCAAGCCCCTTGGGGAGGGCTGCTTCGGCCAGGTG

GTCATGGCGGAGGCCATCGGCATTGACAAGGACCGGGCCGCCAAGCCTGTC

ACCGTAGCCGTGAAGATGCTGAAAGACGATGCCACTGACAAGGACCTGTCG

```
                     -continued
GACCTGGTGTCTGAGATGGAGATGATGAAGATGATCGGGAAACACAAAAAC

ATCATCAACCTGCTGGGCGCCTGCACGCAGGGCGGGCCCCTGTACGTGCTG

GTGGAGTACGCGGCCAAGGGTAACCTGCGGGAGTTTCTGCGGGCGCGGCGG

CCCCCGGGCCTGGACTACTCCTTCGACACCTGCAAGCCGCCCGAGGAGCAG

CTCACCTTCAAGGACCTGGTGTCCTGTGCCTACCAGGTGGCCCGGGGCATG

GAGTACTTGGCCTCCCAGAAGTGCATCCACAGGGACCTGGCTGCCCGCAAT

GTGCTGGTGACCGAGGACAACGTGATGAAGATCGCAGACTTCGGGCTGGCC

CGGGACGTGCACAACCTCGACTACTACAAGAAGACAACCAACGGCCGGCTG

CCCGTGAAGTGGATGGCGCCTGAGGCCTTGTTTGACCGAGTCTACACTCAC

CAGAGTGACGTCTGGTCCTTTGGGGTCCTGCTCTGGGAGATCTTCACGCTG

GGGGGCTCCCCGTACCCGGCATCCCTGTGGAGGAGCTCTTCAAGCTGCTG

AAGGAGGGCCACCGCATGGACAAGCCCGCCAACTGCACACGACCTGTAC

ATGATCATGCGGAGTGCTGGCATGCCGCGCCCTCCCAGAGGCCCACCTTC

AAGCAGCTGGTGGAGGACCTGGACCGTGTCCTTACCGTGACGTCCACCGAC

GAGTACCTGGACCTGTCGGCGCCTTTCGAGCAGTACTCCCCGGGTGGCCAG

GACACCCCCAGCTCCAGCTCCTCAGGGGACGACTCCGTGTTTGCCCACGAC

CTGCTGCCCCCGGCCCCACCCAGCAGTGGGGGCTCGCGGACG
```

Such nucleic acid sequence has been optimized to decrease GC content (while encoding for the native polypeptide sequence) in order to prolong mRNA half life as well as to facilitate sub-cloning.

A "functional equivalent" is a molecule (e.g. a recombinant polypeptide) that retains the biological activity and the specificity of the parent polypeptide. Therefore, the term "functional equivalent of sFGFR3" includes variants and fragments of the polypeptide to which it refers (i.e. the sFGFR3 polypeptide) provided that the functional equivalents exhibit at least one, preferably all, of the biological activities of the reference polypeptide, for instance retains the capacity of binding to the FGFs proteins. As used herein, "binding specifically" means that the biologically active fragment has high affinity for FGFs but not for control proteins. Specific binding may be measured by a number of techniques such as ELISA, flow cytometry, western blotting, or immunoprecipitation. Preferably, the functionally equivalent specifically binds to FGFs at nanomolar or picomolar levels.

Thus, the polypeptide according to the invention encompasses polypeptides comprising or consisting of fragments of the extracellular region of the FGFR3, provided the fragments are biologically active. In the frame of the invention, the biologically active fragment may for example comprise at least 300, 325, 350, consecutive amino acids of the extracellular region of the FGFR3 receptor.

By "biological activity" of a functional equivalent of the extracellular region of the FGFR3 receptor is meant (i) the capacity to bind to FGFs; and/or (ii) the capacity to reduce FGF intracellular signaling (e.g. Erk phosphorylation following FGFR3 receptor activation by its binding with FGFs); and/or (iii) the capacity to restore bone growth in vivo (e.g. in Fgfr3$^{ach/+}$ mice).

The skilled in the art can easily determine whether a functional equivalent of the extracellular region of the FGFR3 is biologically active. To check whether the newly generated polypeptides bind to FGFs and/or reduce FGF intracellular signaling in the same way than the initially characterized polypeptide sFGFR3 (a polypeptide consisting of the sequence depicted in SEQ ID NO: 1) a binding assay, a FGF activity assay or an ERK Activation Assay (see in Example) may be performed with each polypeptide. Additionally, a time-course and a dose-response performed in vitro or in vivo (e.g. by using Fgfr3$^{ach/+}$ mice as described in the Examples section) will determine the optimal conditions for each polypeptide.

Moreover, it should be further noted that functional activation of the FGFR3 receptor may be readily assessed by the one skilled in the art according to known methods. Indeed, since activated FGFR3 receptor is phosphorylated on tyrosine residues located towards the cytoplasmic domain, i.e. on Tyr$^{648}$ and Tyr$^{647}$, functional activation of the FGFR3 receptor may for example be assessed by measuring its phosphorylation.

For instance, analysis of ligand-induced phosphorylation of the FGFR3 receptor can be performed as described in Le Corre et al. (Org. Biomol. Chem., 8: 2164-2173, 2010).

Alternatively, receptor phosphorylation in cells can be readily detected by immunocytochemistry, immunohistochemistry and/or flow cytometry using antibodies which specifically recognize this modification. For instance phosphorylation of FGFR3 on the Tyr$^{648}$ and Tyr$^{647}$ residues can be detected by immunocytochemistry, immunohistochemistry and/or flow cytometry using monoclonal or polyclonal antibodies directed against phosphorylated Tyr$^{648}$ and Tyr$^{647}$-FGFR3.

Further, FGFR3, when associated with its ligand, mediates signaling by activating the ERK and p38 MAP kinase pathways, and the STAT pathway. Therefore activation of FGFR3 receptor can also be assessed by determining the activation of these specific pathways as described by Horton et al. (Lancet, 370: 162-172, 2007)

In one embodiment, the polypeptides of the invention may comprise a tag. A tag is an epitope-containing sequence which can be useful for the purification of the polypeptides. It is attached to by a variety of techniques such as affinity chromatography, for the localization of said peptide or polypeptide within a cell or a tissue sample using immunolabeling techniques, the detection of said polypeptide by immunoblotting etc. Examples of tags commonly employed in the art are the GST (glutathion-S-transferase)-tag, the FLAG™-tag, the Strep-tag™, V5 tag, myc tag, His tag (which typically consists of six histidine residues), etc.

In another embodiment, the polypeptides of the invention may comprise chemical modifications improving their stability and/or their biodisponibility. Such chemical modifications aim at obtaining polypeptides with increased protection of the polypeptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:
  replacement(s) of an amino acid with a modified and/or unusual amino acid, e.g. a replacement of an amino acid with an unusual amino acid like Nle, Nva or Orn; and/or
  modifications to the N-terminal and/or C-terminal ends of the peptides such as e.g. N-terminal acylation (preferably acetylation) or desamination, or modification of the C-terminal carboxyl group into an amide or an alcohol group;
  modifications at the amide bond between two amino acids: acylation (preferably acetylation) or alkylation (preferably methylation) at the nitrogen atom or the alpha carbon of the amide bond linking two amino acids;

modifications at the alpha carbon of the amide bond linking two amino acids such as e.g. acylation (preferably acetylation) or alkylation (preferably methylation) at the alpha carbon of the amide bond linking two amino acids.

chirality changes such as e.g. replacement of one or more naturally occurring amino acids (L enantiomer) with the corresponding D-enantiomers;

retro-inversions in which one or more naturally-occurring amino acids (L-enantiomer) are replaced with the corresponding D-enantiomers, together with an inversion of the amino acid chain (from the C-terminal end to the N-terminal end);

azapeptides, in which one or more alpha carbons are replaced with nitrogen atoms; and/or betapeptides, in which the amino group of one or more amino acid is bonded to the β carbon rather than the α carbon.

In another embodiment, adding dipeptides can improve the penetration of a circulating agent in the eye through the blood retinal barrier by using endogenous transporters.

Another strategy tor improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In still another embodiment, the polypeptides of the invention may be fused to a heterologous polypeptide (i.e. polypeptide derived from an unrelated protein, for example, from an immunoglobulin protein).

As used herein, the terms "fused" and "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. For instance, a recombinant fusion protein may be a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence.

As used herein, the term "sFGFR3 fusion protein" refers to a polypeptide comprising the FGFR3 polypeptide or a functional equivalent thereof fused to heterologous polypeptide. The FGFR3 fusion protein will generally share at least one biological property in common with the FGFR3 polypeptide (as described above).

An example of a sFGFR3 fusion protein is a sFGFR3 immunoadhesin.

It should be further noted that a further aspect of the invention relates to an isolated sFGFR3 immunoadhesin as such as well as to its use as drug.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The immunoglobulin sequence preferably, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In one embodiment, the Fc region is a native sequence Fc region. In another embodiment, the Fc region is a variant Fc region. In still another embodiment, the Fc region is a functional Fc region. The sFGFR3 portion and the immunoglobulin sequence portion of the sFGFR3 immunoadhesin may be linked by a minimal linker. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

Another example of a sFGFR3 fusion protein is a fusion of the sFGFR3 polypeptide with human scrum albumin-binding domain antibodies (AlbudAbs) according to the AlbudAb™ Technology Platform as described in Konterman et al. 2012 AlbudAb™ Technology Platform-Versatile Albumin Binding Domains for the Development of Therapeutics with Tunable Half-Lives The polypeptides of the invention may be produced by any suitable means, as will be apparent to those of skill in the art. In order to produce sufficient amounts of a sFGFR3 or functional equivalents thereof, or a sFGFR3 fusion protein such as a sFGFR3 immunoadhesin for use in accordance with the invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells, HeLa cells, baby hamster kidney cells and many others (e.g. HEK 293 cells). Bacteria are also preferred hosts for the production of recombinant protein, due to the ease with which bacteria may be manipulated and grown. A common, preferred bacterial host is *E coli*.

Moreover, it should be noted that the majority of protein-based biopharmaceuticals bare some form of post-translational modification which can profoundly affect protein properties relevant to their therapeutic application. Protein glycosylation represents the most common modification (about 50% of human proteins are glycosylated). Glycosylation can introduce considerable heterogeneity into a protein composition through the generation of different glycan structures on the proteins within the composition. Such glycan structures are made by the action of diverse enzymes of the glycosylation machinery as the glycoprotein transits the Endoplasmatic Reticulum (ER) and the Golgi-Complex (glycosylation cascade). The nature of the glycan structure (s) of a protein has impact on the protein's folding, stability, life time, trafficking, pharmaco-dynamics, pharmacokinetics and immunogenicity. The glycan structure has great impact on the protein's primary functional activity. Glycosylation can affect local protein structure and may help to direct the folding of the polypeptide chain. One important kind of glycan structures are the so called N-glycans. They are generated by covalent linkage of an oligosaccharide to the amino (N)-group of asparagin residues in the consensus sequence NXS/T of the nascent polypeptide chain. N-glycans may further participate in the sorting or directing of a protein to its final target: the N-glycan of an antibody, for example, may interact with complement components. N-glycans also serve to stabilize a glycoprotein, for example, by enhancing its solubility, shielding hydrophobic patches on its surface, protecting from proteolysis, and directing intra-chain stabilizing interactions. Glycosylation may regulate protein half-life, for example, in humans the presence of terminal sialic acids in N-glycans may increase the half-life of proteins, circulating in the blood stream.

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

A number of yeasts, for example, *Pichia pastoris, Yarrowia lipolytica* and *Saccharomyces cerevisiae* are recently under development to use the advantages of such systems but to eliminate the disadvantages in respect to glycosylation. Several strains are under genetical development to produce defined, human-like glycan structures on a protein. Methods for genetically engineering yeast to produce human-like N-glycans are described in U.S. Pat. Nos. 7,029, 872 and 7,449,308 along with methods described in U.S. Published Application Nos. 20040230042, 20050208617, 20040173826, 20050208617, and 20060286637. These methods have been used to construct recombinant yeast that can produce therapeutic glycoproteins that have predominantly human-like complex or hybrid N-glycans thereon instead of yeast type N-glycans. As previously described, human-like glycosylation is primarily characterized by "complex" N-glycan structures containing N-acetyglusosamine, galactose, fucose and/or N-acetylneuraminic acid. Thus, several strains of yeasts have been genetically engineered to produce glycoproteins comprising one or more human-like complex or human-like hybrid N-glycans such as GlcNAcMan3GlcNAc2.

As used herein, the term "skeletal growth retardation disorder" refers to a skeletal disease characterize by deformities and/or malformations of the bones.

These disorders include, but are not limiting to, skeletal growth retardation disorders caused by growth plate (physeal) fractures, idiopathic skeletal growth retardation disorders and FGFR3-related skeletal diseases.

As used herein, the term "idiopathic skeletal growth retardation disorder" refers to a skeletal disease whose the cause is unknown and for which treatment with exogenous growth hormone (GH), e.g. recombinant human GH (rhGH), for instance has been shown to be ineffective.

In the context of the present invention, the term "FGFR3-related skeletal disease" is intended to mean a skeletal disease that is caused by an abnormal increased activation of FGFR3, in particular by expression of a gain-of-function mutant of the FGFR3 receptor As used herein, the expressions "gain-of-function FGFR3 receptor variant", "gain-of-function mutant of the FGFR3" or "mutant FGFR3 displaying a prolonged activity" are used interchangeably and refer to a mutant of said receptor exhibiting a biological activity (i.e. triggering downstream signaling) which is higher than the biological activity of the corresponding wild-type receptor in the presence of FGF ligand.

The FGFR3-related skeletal diseases are preferably FGFR3-related skeletal dysplasias and FGFR3-related craniosynostosis.

The FGFR3-related skeletal dysplasias according to the invention may correspond to an inherited or to a sporadic disease.

As used herein, the term "FGFR3-related skeletal dysplasias" includes but is not limited to thanatophoric dysplasia type I, thanatophoric dysplasia type II, hypochondroplasia, achondroplasia and SADDAN (severe achondroplasia with developmental delay and acanthosis nigricans).

In a preferred embodiment, the FGFR3-related skeletal dysplasia is caused by expression in the subject of a gain-of-function FGFR3 receptor variant such as defined above.

In a preferred embodiment, the FGFR3-related skeletal dysplasia is an achondroplasia caused by expression of the G380R gain-of-function mutant of the FGFR3 receptor.

Alternatively, the FGFR3-related skeletal dysplasia is an achondroplasia caused by expression of the G375C, G346E or S279C of the FGFR3 receptor.

It should be further noted that achondroplasia caused by another mutant of the FGFR3 receptor which would be identified in the future is also encompassed.

In a preferred embodiment, the FGFR3-related skeletal dysplasia is a hypochondroplasia caused by expression of the N540K, K650N, K650Q, S84L, R200C, N262H, G268C, Y278C, V381E, gain-of-function mutant of the FGFR3 receptor.

In a preferred embodiment, the FGFR3-related skeletal dysplasia is a thanatophoric dysplasia type I caused by expression of a gain-of-function mutant of the FGFR3 receptor chosen from the group consisting of R248C, S248C, G370C, S371C, Y373C, X807R, X807C, X807G, X807S, X807W and K650M FGFR3 receptors.

In a preferred embodiment, the FGFR3-related skeletal dysplasia is a thanatophoric dysplasia type II caused by expression of the K650E gain-of-function mutant of the FGFR3 receptor.

In a preferred embodiment, the FGFR3-related skeletal dysplasia is a severe achondroplasia with developmental delay and acanthosis nigricans caused by expression of the K650M gain-of-function mutant of the FGFR3 receptor.

The present invention also provides a method for preventing or treating a skeletal growth retardation disorder comprising the step of administering a therapeutically effective amount of a soluble FGFR3 (sFGFR3) polypeptide to a subject in need thereof.

By a "therapeutically effective amount" of a sFGFR3 as above described is meant a sufficient amount of the antagonist to prevent or treat a FGFR3-related skeletal disease (e.g. achondroplasia). It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

As used herein, the term "subject" denotes a human or non-human mammal, such as a rodent, a feline, a canine, an equine, or a primate. Preferably, the subject is a human being, more preferably a child (i.e. a child who is growing up).

It should be reminded that the cartilaginous matrix of the growth plate is less dense in a newborn or in a child than in an adult. Therefore, without wishing to be bound by the theory, one can expect that the polypeptide of the invention will better penetrate said cartilaginous matrix in a newborn or a child.

In one embodiment, the subject has been diagnosed as suffering from a FGFR3-related skeletal disease. As previously described, the FGFR3-related skeletal disease is caused by expression in the subject of a constitutively active FGFR3 receptor variant such as the G380R constitutively active mutant.

In the context of the invention, the term "treating" is used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

As used herein, the term "preventing" intends characterizing a prophylactic method or process that is aimed at delaying or preventing the onset of a disorder or condition to which such term applies.

Pharmaceutical Compositions of the Invention

The isolated soluble FGFR3 polypeptide (sFGFR3) as described above may be combined with pharmaceutically acceptable excipients, and optionally sustained-release matrices, such as biodegradable polymers, to form therapeutic compositions.

Accordingly, the present invention also relates to a pharmaceutical composition comprising an isolated sFGFR3 polypeptide according to the invention and a pharmaceutically acceptable carrier.

The present invention further relates to a pharmaceutical composition for use in the prevention or treatment of a skeletal growth retardation disorder comprising a sFGFR3 according to the invention and a pharmaceutically acceptable carrier.

In one embodiment, the skeletal growth retardation disorder is an idiopathic growth retardation disorder.

In another embodiment, the skeletal growth retardation disorder is a FGFR3-related skeletal disease.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc. The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

To prepare pharmaceutical compositions, an effective amount of a polypeptide according to the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The polypeptides according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropyl amine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the subject.

Another aspect of the present invention is a pharmaceutical composition for use in the prevention or treatment of a skeletal growth retardation disorder comprising an isolated sFGFR3 polypeptide or a functional equivalent thereof according to the invention and a pharmaceutically acceptable carrier.

In one embodiment, the skeletal growth retardation disorder is an idiopathic growth retardation disorder.

In another embodiment, the skeletal growth retardation disorder is a FGFR3-related skeletal disease.

The present invention also provides a method for preventing or treating a skeletal growth retardation disorder comprising a step of administering a pharmaceutical composition comprising a therapeutically effective amount of a sFGFR3 polypeptide or a functional equivalent thereof and a pharmaceutically acceptable carrier to a subject in need thereof.

The invention will be further illustrated by the following figures and examples. However, these examples and figures should not be interpreted in any way as limiting the scope of the present invention.

FIGURES

FIG. 1: Effective FGF binding and decreased Erk phosphorylation in ATDC5 cells in presence of FLAG-sFGFR3. (A) Fixed amounts of human or murine basic FGF (100 ng) were incubated with increasing concentrations of FLAG-sFGFR3. After 2 h, remaining unbound FGFs were detected by ELISA. Linear regression analysis showed no statistical differences between the two slopes. hFGF, human FGFb; mFGF, mouse FGFb. Experiment was performed in triplicate and repeated five times. (B) Erk phosphorylation was evaluated by immunoblotting on ATDC5 cells following incubation with increasing doses of FLAG-sFGFR3. The graph represents the phosphorylation variations in percentage compared to phosphorylation levels in untreated cells. Experiments were repeated six times. Following verification of normality, statistical comparisons were performed using a one way ANOVA. *$p<0.05$, ***$p<0.001$. Values represent mean±SD.

Figure 2:
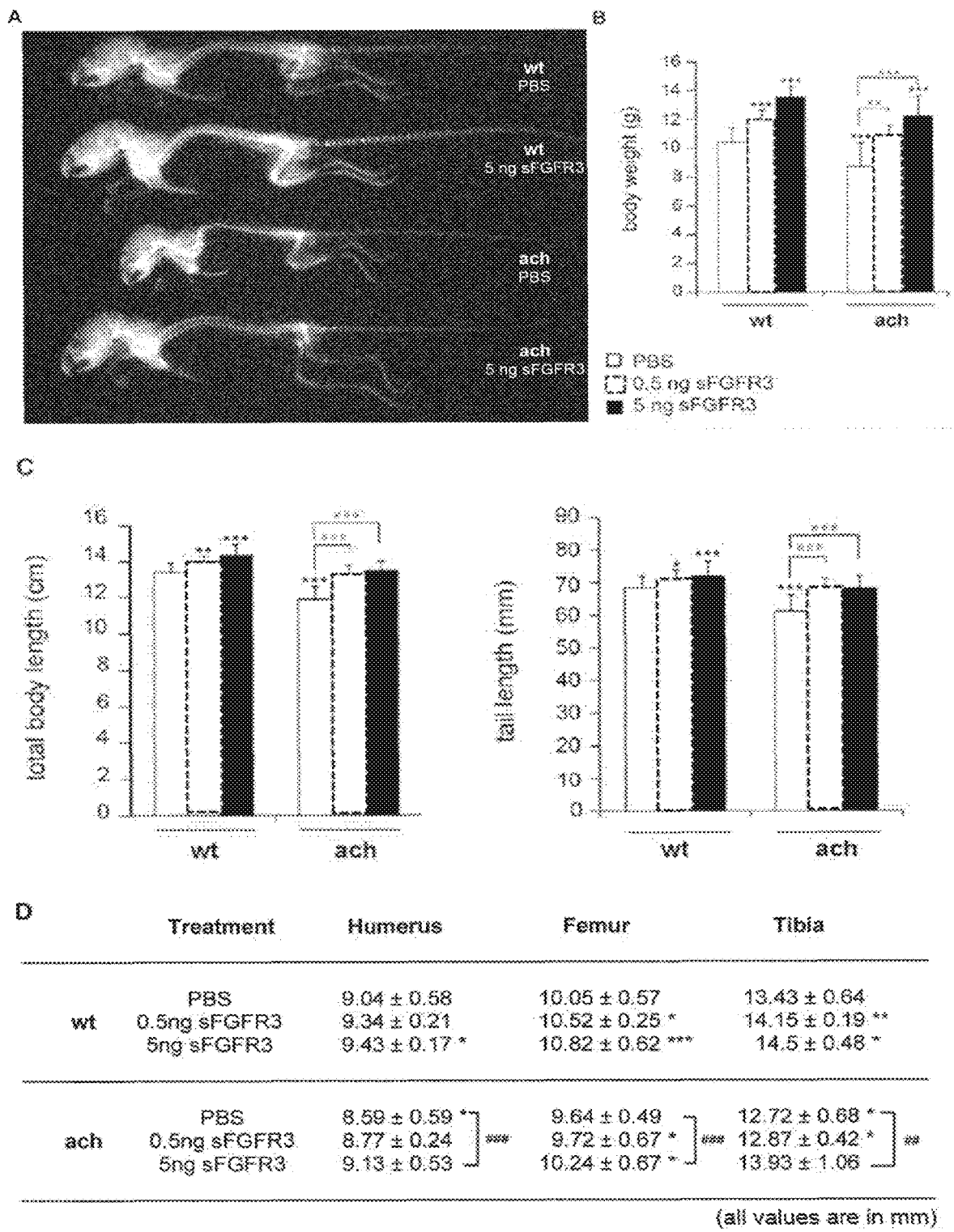

FIG. 2: FLAG-sFGFR3 treatment effect on overall skeletal growth. (A) X-ray radiographies illustrating treatment effect on skeletal growth. Showed skeletons are representative of wt and Fgfr3$^{ach/+}$ mice that received subcutaneous injection of PBS or 5 ng FLAG-sFGFR3. Growth was characterized by body weight (B), body and tail lengths (C), and long bone measurements (D). (Data followed normal distribution; a Student's t test was used to compare data to measurements obtained on untreated mice. n per group are shown in Table 1; *$p<0.05$; $p<0.01$; *$p<0.001$ versus untreated wt; ##$p<0.01$; ###$p<0.001$ versus untreated Fgfr3$^{ach/+}$ mice. wt: wildtype mice; ach: Fgfr3$^{ach/+}$ mice FIG. 3: Effect of FLAG-sFGFR3 treatment on vertebrae maturation. (A) The kyphosis index (KI) was measured from radiographs of mice positioned in right lateral recumbency. As defined by Laws et al. (28), line AB is the length of a line drawn from posterior edge of C7 to the posterior edge of L6. Line CD is the distance from line AB to the dorsal border of the vertebral body farthest from that line. Clinically, a kyphosis is characterized with KI<4. (B) Photographs of representative vertebrae from untreated wt, untreated Fgfr3$^{ach/+}$ mice and transgenic mice receiving 5 ng FLAG-sFGFR3. In the table are indicated the percentage of animals in the different treatment groups with immature C7, T11 and lumbar vertebrae. $^§$Lumbar compressions were characterized by paraplegia or locomotion deficiency. Data followed normal distribution; a Student's t test was used to compare data to measurements obtained on untreated mice. n per group arc shown in Table 1; *$p<0.05$; ***$p<0.001$ versus untreated wt; ##$p<0.01$; ###$p<0.001$ versus untreated Fgfr3$^{ach/+}$ mice. wt: wild type mice; ach: Fgfr3$^{ach/+}$ mice.

Figure 4:
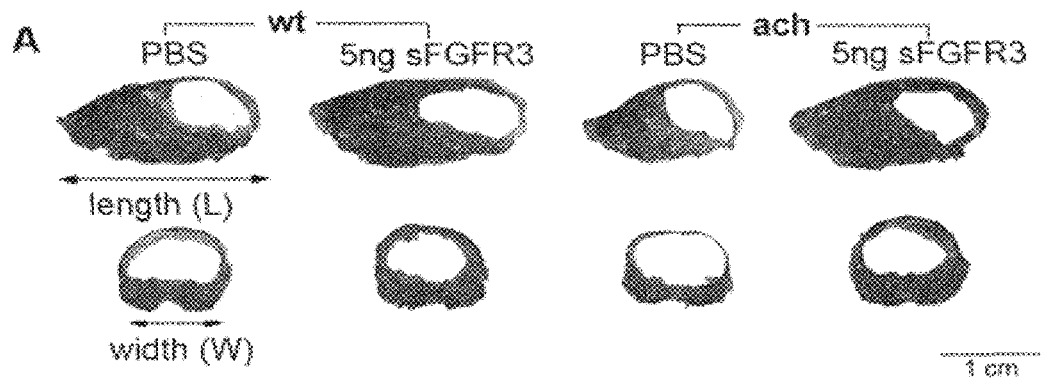
Figure 4:
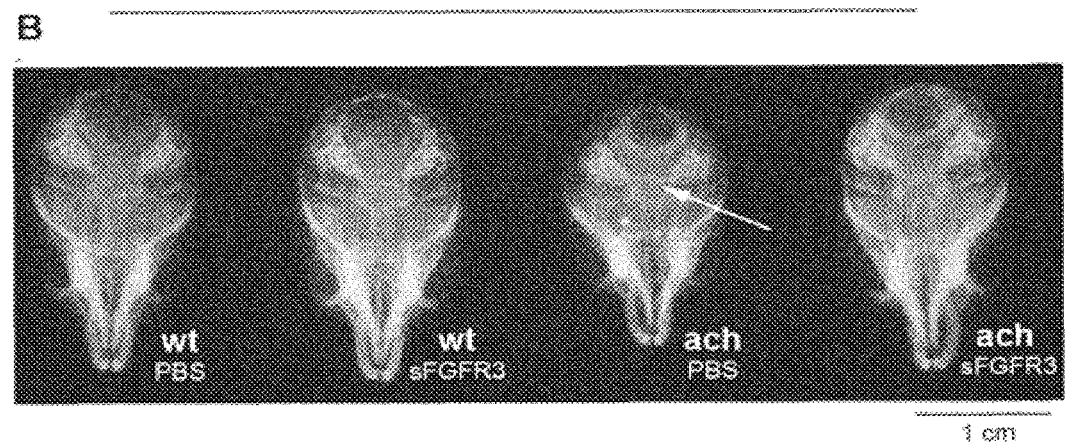

FIG. 4: FLAG-sFGFR3 treatment effects on skull development. (A) Skull length (L) and width (W) were measured and the ratio L/W calculated. Statistical analysis was performed using a Student's t test following verification of normal variance and distribution. n per group are shown in Table 1; $p<0.001$ versus untreated wt; #$p<0.05$ versus untreated Fgfr3$^{ach/+}$ mice. (B) Representative X-rays of skulls from wt and Fgfr3$^{ach/+}$ mice that received either PBS or 5 ng FLAG-sFGFR3. They show treatment prevention of premature closure of cranial synchondrose typically observed on Fgfr3$^{ach/+}$ mice. This is indicated by the arrowhead. wt: wildtype mice; ach: Fgfr3$^{ach/+}$ mice.

EXAMPLE

Material & Methods sFGFR3 subcloning and recombinant protein production: To facilitate sub-cloning, full-length cDNA sequence encoding the FGFR3ΔTM (2.1 kb) (35), a generous gift from Dr. Kurokawa-Seo, Kyoto Sangyo University, Japan, was optimized to decrease GC content while encoding for the original protein sequence (GeneOptimizer® process, GeneArt). The synthesized fragment was subcloned into pFLAG-CMV3_G727 (Sigma Aldrich) using HindIII and KpnI cloning sites. Plasmid DNA was purified from transformed bacteria and concentration determined by UV spectroscopy. The final construct was verified by sequencing. The sequence homology within the used restriction sites was 100%.

Recombinant FLAG-sFGFR3 protein was produced by transient transfection using GeneJuice transfection reagent (Merck Millipore) in HEK 293 cells allowing all necessary post-translational modifications. Each transfection was performed in a cell factory (High flask T600, Merck Millipore) with 80% confluent HEK 293 in 100 ml DMEM without phenol red (Gibco, Life Technologies) supplemented with glutamine 2 mM (Gibco, Life Technologies) and 1% antibiotics (Gibco, Life Technologies). 600 µl GeneJuice and 240 µg pFLAG-sFGFR3 were resuspended in 30 ml OptiMEM (Gibco, Life Technologies), incubated 30 min at room temperature, and then incubated for 4 h onto the cells at 37° C. in 5% $CO_2$. Medium was then replaced by 120 ml DMEM without phenol red, supplemented with glutamine 2 mM and 1% antibiotics. After 72 h, production medium was filtrated using 0.22 µm filters and concentrated on Amicon Ultra-15 60 kDa (Merck Millipore). Recombinant protein was then purified on an affinity column (ANTI-FLAG M2 Affinity Gel, Sigma Aldrich) according to the manufacturer's instructions. FLAG-sFGFR3 amounts were measured by specific ELISA (R&D Systems) according to the manufacturer's instructions. FLAG-sFGFR3 was then stored at a concentration of 0.5 µg/ml in 50% glycerol solution.

FLAG-sFGFR3 incubation with FGF: Fixed amounts of human or murine FGFs (100 pg) (R&D Systems) were incubated for 2 h at 37° C. with increasing doses of FLAG-sFGFR3 (0 to 250 ng/ml) in PBS 1% BSA. Specific commercial ELISA kits (R&D Systems) were used to quantify remaining unbound FGFs. All experiments were performed in triplicates and repeated five times.

Half-life of sFGFR3: To determine the half-life of sFGFR3, 8 week old WT mice received an intravenous bolus of 50 mg/kg of FLAG-sFGFR3. At 15 min, 1 h, 3 h, 6 h, and 24 h, blood was harvested by retro-orbital puncture using heparin catheter (n=4). Concentration of FLAG-sFGFR3 was measured by anti FLAG ELISA (Sigma). The half-life of the terminal phase was calculated using the following parmacokinetic equation $t_{1/2}=0.693/\lambda_z$, where 0.693 is the natural logarithm of 2 and $\lambda_z$, the slope of the terminal phase.

Immunoblotting analysis: Immunoblotting was performed following incubation of several doses of FLAG-sFGFR3 on ATDC5 cells. For this, ATDC5 cells were plated at a density of $2 \times 10^6$ in 6 well plates and, following adhesion, cultured for 48 h in 0.5% BSA in DMEM-F12 (Gibco, Life Technologies) containing 1% antibiotics. Cells were then cultured for 10 min with 100 pg/ml murine FGF pre-incubated for 2 h at 37° C. with increasing doses of FLAG-sFGFR3 (0, 12.5, 125, 1250, 12500 pg/ml). At the end of the incubation period, remaining unbound FGFs were measured by specific ELISA (R&D Systems). Cells were then solubilized in lysis buffer (20 mM Tris, pH 7.4, 150 mM NaCl, 10 mM EDTA, 150 mM NaF, 2 mM sodium orthovanadate, 10 mM pyrophosphate, proteases inhibitors, and 1% Triton X-100) for 45 min at 4° C. Lysates were cleared (14 000 rpm, 10 min) and proteins were separated by SDS-PAGE and immunoblotted as previously described (36). The proteins were probed with anti-phospho p42/44 MAPK (4370S, Cell Signaling), anti-total p42/44 MAPK (4696S, Cell Signaling) and anti-hsp60 (sc1722, Santa Cruz Biotechnology) antibodies (1 µg/ml). All experiments were performed six times.

Immunohistochemistry of FLAG-sFGFR3: Immunohistochemistry of FLAG-sFGFR3 was performed on tibiae of 3 day old Fgfr3$^{ach/+}$ mice and their wildtype littermates. For this, following decapitation of newborn mice, tibiae were carefully harvested and incubated in 24 well plates in presence of 5 ng FLAG-sFGFR3 for 24 h at 37° C. in 5% $CO_2$. Tibiae were then rinsed in PBS and fixed in 10% formalin for 24 h. Following decalcification in EDTA for 2 days, bones were paraffin embedded and 5 µm sections were incubated with 5 µg/ml anti-FLAG M2-FITC monoclonal antibody (Sigma Aldrich). Sections were counterstained with Hoechst solution and visualized under fluorescent microscopy. An anti-IgG antibody was used as negative control.

Animals and treatments: The Principles of Laboratory Animal Care (NIH publication no. 85-23, revised 1985; grantsl.nih.gov/grants/olaw/references/phspol.htm) and the European commission guidelines for the protection of animals used for scientific purposes (ec.europa.eu/environment/chemicals/lab_animals/legislation_en.htm) were followed at all times. All procedures were approved by the Institutional Ethic Committee for the use of Laboratory Animals (CIEPAL Azur) (approval #NCE-2012-52).

Experiments were performed on transgenic Fgfr3ach/+ animals in which expression of the mutant FGFR3 is driven by the Col2a1 promoter/enhancer (22). Mice were exposed to a 12 h light/dark cycle and had free access to standard laboratory food and water. All measurements and analyses were performed blinded and genotypes were analyzed after all analyses were done by PCR of genomic DNA which amplify 360 bp of the FGFR3 transgene (22). Two doses of FLAG-sFGFR3 (0.5 ng and 5 ng in 10 µl PBS with 50% glycerol) were tested. At day 3, all newborn mice from a single litter received the same dose. Control litters received 10 µl of PBS containing 50% glycerol. Subcutaneous injections were thereafter done twice a week for three weeks, alternatively on the left and right sides of the back. Mice were observed daily with particular attention to locomotion and urination alterations. At day 22, all animals but two litters per group were sacrificed by CO2 asphyxation; genus and genotypes were determined. Body weights were measured. Blood was harvested by cardiac puncture and mixed with 50 µl 0.5M EDTA; half of the samples were centrifuged for a biochemical assessment using a Beckman AU 2700 Analyzer (electrolytes (Na+, K+, Cr), lactate dehydrogenase (LDH), cholesterol, creatinin, creatinin kinase (CK), aspartate aminotransferase (AST), alanine aminostransferase (ALT), amylase, total bilinbin (BLT)); the other half was analyzed without centrifugation for blood numeration (Hemavet 950FS, Mascot Hematology). Cadavers were carefully skinned and eviscerated and skeletal measurements (body and tail lengths) were obtained using an electronic digital caliper (Fisher Scientific). Total body length was measured from the nose to the end of the last caudal vertebra; tail was measured starting at the first caudal vertebra. Organs (heart, lungs, liver, kidneys, spleen) were harvested, weight and stored in 10% formalin for further histological analysis using standard paraffin-embedded techniques. X-rays of all skeletons were taken using a Faxitron X-ray machine (Edimex). Using an established method (28), kyphotic index were measured for each animals on the X-rays. Cleared skeletons were then stained simultaneously with alcian blue and alizarin red using standard procedures and stored in glycerol prior to analysis. Stained long bones (tibiae, femurs, humerus) were dissected and measured using an electronic digital caliper; vertebrae and skulls were also dissected and analyzed.

Breeding was set up to theoretically generate litters with half wildtype and half heterozygous Fgfr3$^{ach/+}$ mice. To avoid bias due to variations of phenotype penetrance, experiments were performed on at least 2 litters (one treated and one control) arising from the same breeders. A total of 15, 9 and 11 litters representing a total of 312 pups were treated with PBS, 0.5 ng or 5 ng FLAG-sFGFR3, respectively. The n per group is presented in Table 1.

Effect of FLAG-sFGFR3 on the fertility of treated animals: Animals from the litters that were not used for skeletal measurements were kept until breeding age was reached. At age 8 week, they were then mated with 8 week old FVB/N mice from Charles River. Newborn mice were counted at birth for each treated and control male and female and compared with fertility statistics of the previous generation. At age 22, offspring were euthanized and growth was evaluated as described above.

Proliferation and differentiation assays: sFGFR3 effect on proliferation was determined on ATDC5 cells. For this, ATDC5 cells were plated at a density of $5 \times 10^4$ in 24 well plates and cultured tor 48 h in DMEM-F12 0.5% BSA (Life Technologies). Cells were then challenged for 72 h with 100 pg/ml of FGF2, FGF9 or FGF18 in presence of 0 or 20 ng/ml of FLAG-sFGFR3. Proliferation was evaluated using the MTT (3-(4,5-dimethylthiazol-2-yl)-2,5-diphenyltetrazolium bromide) proliferation assay by measurement of absorbance at 540 nm.

To determine treatment effect on chondrocyte differentiation, sub-confluent ATDC5 cells were incubated in 24 well plates for 7 days in chondrocyte differentiation medium (37.5 µg/ml L-ascorbic acid; 1 mM sodium pyruvate; 1% Insulin-transferrin-sodium selenite; 100 nM dexamethasone in DMEM F12) in the presence of 100 pg/ml of FGF and 0 or 20 ng/ml FLAG-sFGFR3. After 7 days in culture, half of the wells were stained with Alcian blue, pH 2.5, in 3% acetic acid. In the remaining wells, total RNA was extracted using an RNeasy Mini Kit (Qiagen). Total RNA (1 µg) was reverse-transcribed, and real-time PCR was performed (ABI PRISM 7500). The TaqMan gene expression assays were purchased from Applied Biosystems: Col10al (Mm00487041_ml), Col2al (Mm01309565_ml), Sox9 (Mm00448840_ml), Fgfr3 (Mm00433294_ml), RPLP0 (Ribosomal Phosphoprotein Large P0, Mm00725448_sl). Gene expression values were normalized to the expression value of the housekeeping gene RPLP0 and calculated based on the comparative cycle threshold Ct method ($2^{-\Delta Ct}$) as described previously.

Statistical analysis: All experiments and data measurements were performed by blind experimenters at all times. Statistical analyses were performed with GraphPad Prism 6.0 software. To determine the statistical tests to be used, necessary assumptions were verified. To verify normality and equal variance, an Agostino and Pearson omnibus normality test and a Brown-Forsythe test were performed, respectively. Because all skeletal measurements data sets fulfilled normality and equal variance requirements, two-tailed Student's t test for comparisons of two independent groups were used in the different statistical analyses. Comparison of mortality data between treated and control groups was done using a Kruskal-Wallis test. Comparison of FLAG-sFGFR3 binding to human and murine FGFs was done by linear regression. Immunoblotting data distribution followed normality and were thus analyzed using a one-way ANOVA using a Holm-Sidak's multiple comparisons test. For organ weight correlation analyses, Pearson or Spearman tests were used when data sets followed or not normal distribution, respectively. All statistical tests were considered significant at a p<0.05 level of error. In all figures, values of p are show n as follows: *p<0.05; p<0.01; *p<0.001. Data are presented as means±SD.

Results

FLAG-sFGFR3 effectively binds FGFs and decreases MAPK signaling in ATDC5 cells: A soluble form of FGFR3 was produced by transient transfection of a plasmid encoding the FGFR3ΔTM sequence. In order to detect recombinant soluble FGFR3 in vivo, the inventors used a soluble form of FGFR3 labeled with a FLAG tag. This tag was used because of the availability of reagents for its purification and its detection (23, 24). It has also already been used in vivo without inducing premature elimination of the tagged protein by the immune system (25, 26). In the present experiments, recombinant FLAG-sFGFR3 was produced by transient transfection in human embryonic kidney (HEK) 293 cells, allowing for all necessary post-translational modifications, purified using affinity column and stored at a concentration of 0.5 µg/ml in 50% glycerol. In mice, the half-life of sFGFR3 is 16 hours.

To verify that FLAG-sFGFR3 effectively bound free FGFs, fixed amounts of human FGFs were incubated with increasing quantities of FLAG-sFGFR3. As seen in FIG. 1A, FLAG-sFGFR3 effectively bound hFGF in a dose-dependent manner. The FGFR3ΔTM sequence used is of human origin, the inventors verified that it could also bind murine FGF. Similar results were obtained and FLAG-sFGFR3 was able to bind similar amounts of murine FGFs. This was expected since there is a 90% sequence homology between murine and human FGFR3. sFGFR3 competed for hFGF binding with endogenous FGFR3 on murine chrondrocytes (ATDC5 cells), demonstrating the decoy receptor mechanism.

The inventors then verified that the complexation of FGF with FLAG-sFGFR3 resulted in a decreased intracellular FGF signaling on Erk phosphorylation. ATDC5 cells were used as a murine chondrocytic cell line to study chondrocyte biology (27). As seen FIG. 1B, significant decrease in Erk phosphorylation was seen in relation with the dose of FLAG-sFGFR3. This was correlated with a decrease of free FGFs in the conditioned medium, similar to that observed in FIG. 1A. These results demonstrate that FLAG-sFGFR3 effectively binds FGFs of human and murine origin thus decreasing FGF intracellular signaling. sFGFR3 treatment also restored proliferation and differentiation of mouse ATDC5 cells and significantly increased collagen type 2, collagen type 10 and Sox 9 gene expression relative to FGF alone (P<0.05, Student's t test). No effect on proliferation, differentiation, or gene expression was observed in presence of the control protein.

FGF-independent mechanisms have also been explored. Stat1 was not phosphorylated in Fgfr3$^{ach/+}$ chondrocytes treated with sFGFR3. Moreover, fgfr3 gene expression was unchanged from FGF-only controls by sFGFR3 treatment in chondrocytes isolated from Fgfr3$^{ach/+}$ animals. Together, these data suggest that sFGFR3 effects are mediated only through FGF-dependent pathways.

Soluble FGFR3 increases survival of Fgfr3$^{ach/+}$ mice and effectively restores bone growth in Fgfr3$^{ach/+}$ mice: Prior to test FLAG-sFGFR3 treatment effect in vivo, the inventors verified that it could penetrate the dense cartilaginous matrix of the growth plate and reach target chondrocytes. Long bones isolated from three day old Fgfr3$^{ach/+}$ mice and their wildtype (wt) littermates were incubated for 24 h in presence of 5 ng FLAG-sFGFR3. As seen in FIG. 2, the recombinant protein was detected within the matrix, near the chondrocytes of the tibial growth plate of wt and Fgfr3$^{ach/+}$ mice, showing that the protein efficiently penetrates the dense cartilaginous matrix of the growth plate and reach target chondrocytes.

To evaluate the biological effects of FLAG-sFGFR3 treatment on skeletal bone growth in Fgfr3$^{ach/+}$ mice, all newborn mice from one litter received the same treatment without knowing their phenotype. They received a subcutaneous injection of 0.5 or 5 ng FLAG-sFGFR3, or PBS in control groups, twice a week during 3 weeks. The first observation was the significant reduction in mortality in treated compared to untreated litters. At the end of the treatment period, control groups contained about a third of transgenic animals alive while in both treated groups, there were approximately 50% wt mice and 50% Fgfr3$^{ach/+}$ (Table 1). Moreover, in the control litters, 31% of animals died prior to the end of the experiments compared to 11.8% and 6.7% in the 0.5 ng and 5 ng FLAG-sFGFR3 treated litters, respectively. This reduction in group size was due to premature death or euthanasia of paraplegic animals. When it was possible, autopsy was performed and confirmed death due to respiratory failure as seen by the presence of blood within the lungs. Two animals died consequently to bowel obstruction. All of these animals were Fgfr3$^{ach/+}$, as confirmed by genotyping. No wild-type animal died prematurely. It is noteworthy to emphasize that in the control group, the majority of affected Fgfr3$^{ach/+}$ mice died from respiratory failure, while in the 5 ng FLAG-sFGFR3 treatment group, they mostly suffered from paraplegia and only few had respiratory distress (Table 1). Altogether these data indicate that with treatment fewer animals died, and those who died had a less severe phenotype.

TABLE 1

Number of pups in the different treatment groups at day 3 and day 22.

|  | Number of litters per group | Number of pups Day 3 | Number of pups Day 22 | % dead animals before day 22 (cause of death) |
|---|---|---|---|---|
| PBS | 15 | 132 | 91 (wt: 67; ach: 24) | 31% (23 by respiratory failure, 2 by bowel occlusion, 16 by paraplegia) |
| 0.5 ng sFGFR3 | 9 | 76 | 67 (wt: 31; ach: 36) | 11.8% ** (4 by respiratory failure, 5 by paraplegia) |
| 5 ng sFGFR3 | 11 | 104 | 97 (wt: 47; ach: 50) | 6.7% ** (1 by respiratory failure, 6 by paraplegia) |

Litters were considered as single entities and all newborn mice from the same cage received the same treatment. Dead and alive animals were counted daily. Autopsy revealed death by respiratory failure and bowel occlusion for 2 animals. Animals with paraplegia were euthanized upon discovery and recorded in the dead animal group. All dead animals were Fgfr3$^{ach/+}$. Statistical comparison versus control group was done using the Kruskal-Wallis test. ** $p < 0.01$. wt: wildtype mice; ach: Fgfr3$^{ach/+}$ mice.

At day 22, time of weaning, animals were sacrificed and their growth was evaluated. The inventors first confirmed that there was no statistical difference between males and females (Table S1) and regrouped them for all subsequent analyses. As illustrated in FIG. 2A, FLAG-sFGFR3 treatment had an effect on overall skeletal growth. While Fgfr3$^{ach/+}$ mice were in average 20% lighter than their wt littermates, animals treated with FLAG-sFGFR3 displayed a dose dependent increase in their body weight, reaching up to 33% of the weight of untreated transgenic mice (FIG. 2B). A dose dependent treatment effect was also observed on the weight of wt animals. As seen in FIG. 2C, treatment induced a dose dependent increase in body and tail lengths of both Fgfr3$^{ach/+}$ and wt animals. Treated transgenic mice had a stature that was not significantly different from that of untreated wt controls, reaching up to 10% of the lengths of untreated Fgfr3$^{ach/+}$ animals at the high dose correcting the initial discrepancy between transgenic and wt mice.

Similar results were obtained on long bone lengths. Humerus, femurs and tibiae from treated Fgfr3$^{ach/+}$ mice were longer than those of untreated transgenic mice and were statistically identical to the lengths of wt bones (FIG. 2D). FLAG-sFGFR3 treatment also had a dose dependant effect on the growth of long bones from wt mice. Histology confirmed treatment effect on chondrocyte maturation. Treated Fgfr3$^{ach/+}$ mice exhibited organized and hypertrophic chondrocytes in their growth plates similarly to wt mice.

sFGFR3 treatment also corrected rib cage development in Fgfr3$^{ach/+}$ mice. Altogether, these results show that following chronic subcutaneous administration of FLAG-sFGFR3 to neonate Fgfr3$^{ach/+}$ mice, normal bone growth was restored and that it was also effective on skeletal growth of animals that do not trigger an FGFR3 activating mutation. Indeed, Fgfr3$^{ach/+}$ and WT mice treated with sFGFR3 showed greater sternum ossification and lengths compared with vehicle-treated animals in their respective groups.

TABLE S1

Statistical comparison of body measurements between male and female in the different treatment groups.

|  |  |  | n | Body weight (g) | Body length (mm) | Tail length (mm) | male vs female |
|---|---|---|---|---|---|---|---|
| PBS | wt | male | 41 | 11.09 ± 1.26 | 132.43 ± 5.45 | 70.49 ± 3.65 | ns |
|  |  | female | 26 | 10.67 ± 1.99 | 134.04 ± 6.76 | 71.76 ± 4.60 |  |
|  | ach | male | 13 | 9.18 ± 1.82 | 120.56 ± 5.71 | 64.36 ± 2.52 | ns |
|  |  | female | 11 | 8.14 ± 1.55 | 113.95 ± 8.22 | 60.03 ± 3.79 |  |
| 0.5 ng sFGFR3 | wt | male | 12 | 12.31 ± 1.27 | 134.55 ± 7.98 | 73.94 ± 6.35 | ns |
|  |  | female | 19 | 12.03 ± 1.18 | 134.59 ± 6.46 | 72.25 ± 4.51 |  |
|  | ach | male | 19 | 10.50 ± 1.19 | 126.78 ± 9.3 | 69.48 ± 6.64 | ns |
|  |  | female | 17 | 9.34 ± 1.47 | 121.49 ± 10.01 | 65.33 ± 7.96 |  |
| 5 ng sFGFR3 | wt | male | 23 | 13.29 ± 1.48 | 141.47 ± 6.77 | 74.76 ± 5.42 | ns |
|  |  | female | 24 | 12.13 ± 1.85 | 138.73 ± 8.21 | 74.01 ± 6.01 |  |
|  | ach | male | 13 | 11.41 ± 3.14 | 130.43 ± 13.11 | 69.15 ± 9.07 | ns |
|  |  | female | 37 | 10.72 ± 2.19 | 127.59 ± 11.58 | 67.43 ± 7.95 |  |

Following 3 weeks of treatments (PBS, 0.5 ng or 5 ng FLAG-sFGFR3), animals were sacrificed at age 22 days. Body weight, body length and tail length were measured. Genus and genotypes were determined. Following verification of normality variation in each data set, measurements were compared between males and females within the same treatment and genotype group. Data followed normal distribution; a Student's t test was used to compare data to measurements obtained on untreated mice. No statistical difference was found in any group. ns = non significant, wt: wildtype mice; ach: Fgfr3$^{ach/+}$ mice.

Figure 3:
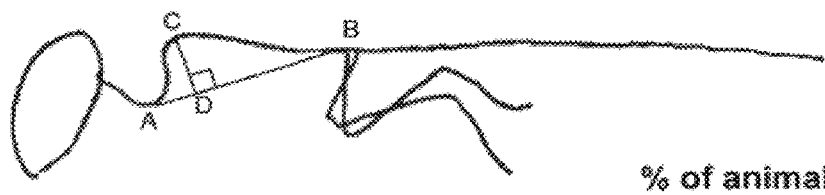
Figure 3:
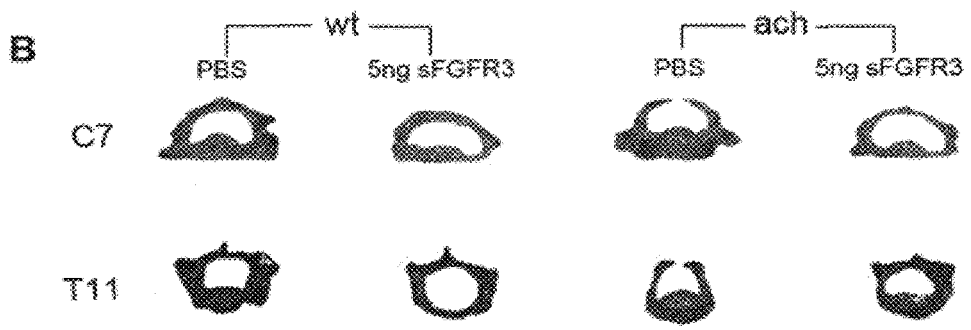

FLAG-sFGFR3 treatment decreases spinal and skull deformities associated with achondroplasia in Fgfr3$^{ach/+}$ mice: In Fgfr3$^{ach/+}$ mice, spinal abnormalities are recognized in particular by the presence of a kyphosis that can be characterized by the calculation of a kyphotic index (KI). In this scoring system, established by Laws et al. (28), mice with a KI<4.0 present a kyphosis (for more details, please see legend of FIG. 3). In the present study, while no wt animals presented a spinal deformity, 80% of untreated Fgfr3$^{ach/+}$ mice displayed cervical kyphosis with an average KI of 3.46±0.65 (FIG. 3A). With FLAG-sFGFR3 treatment, this percentage significantly decreased to 17% and 6% in the 0.5 ng and 5 ng groups, respectively.

To further characterize vertebral maturation, the inventors analyzed ossification of C7 and T11. As seen FIG. 3B, on untreated Fgfr3$^{ach/+}$ mice, the 7$^{th}$ cervical and the 11$^{th}$ thoracic were not fused at the midline in 88.9% and 70.1%, respectively. Following treatment, maturation was restored as seen by the decrease in the number of immature vertebrae. No wt animals in any groups presented immature vertebrae.

Similar to achondroplasia patients that typically have enlarged heads, Fgfr3$^{ach/+}$ mice suffer from skull deformities. While cranium width (W) is not statistically different between transgenic and wt mice (10.35±0.28 mm vs 10.17±0.32 mm, respectively), the length (L) is significantly shorter in Fgfr3$^{ach/+}$ mice (18.11±0.75 mm vs 20.05±0.51 mm in wt mice, respectively). This leads to a L/W ratio equal to 1.75±0.77 in untreated Fgfr3$^{ach/+}$ mice and equal to 1.94±0.05 in control wt mice (FIG. 4A). FLAG-sFGFR3 treatment induced a dose-dependent correction of the cranium length, and the L/W ratio was not significantly different from that of untreated wt at the highest dose of FLAG-sFGFR3.

As seen in FIG. 4B, treatment also prevented the premature closure of cranial synchondrose typically observed in Fgfr3$^{ach/+}$ mice.

Altogether, these results show that FLAG-sFGFR3 treatment is effective at preventing the development of skeleton deformities associated with achondroplasia.

No toxicological effects are detected in treated animals: Because the inventors are using a systemic approach to deliver recombinant soluble FGFR3, they paid a particular attention to possible unwanted side effects. They analyzed organs of all 255 animals, performed biochemical and numeration blood tests and verified fertility of some treated animals (two litters per group) including normality of their offspring.

Potential treatment side effects were first evaluated on several organs (liver, lung, heart, spleen, kidneys) at the time of sacrifice. Organs were observed macroscopically, weighted and randomly analyzed microscopically by histology. None of the 255 animals that received chronic subcutaneous injections of FLAG-sFGFR3 or PBS presented macroscopic abnormalities. Histology was performed on randomly selected organs in all groups and data were analyzed blindly by an anatomopathologist. No signs of toxicity were observed on any histological slides. In all control groups, organ weights were correlated with the mouse body weight (Table 2). In the treated groups, organs increased with enhanced bone growth. As an example, the lungs of untreated Fgfr3$^{ach/+}$ mice were 156.0±88.7 mg. They increased to 172.5&±67.5 mg in the 5 ng treatment group, reaching the weight of lungs in untreated wt mice (170.5±36.3 mg). Similar results were found for all organs and this weight augmentation was statistically correlated with body weight increase in all groups (Table 2). To evaluate organ functions, they performed biochemical blood tests including electrolytes titration, liver, kidney and spleen enzymes assays. All tests proved to be statistically identical between Fgfr3$^{ach/+}$ and wt animals in the treated and control groups (Table S2). Blood counts were also analyzed and similarly, no differences between blood formulations were noticed between treated and control groups (Table S3).

TABLE 2

Coefficient correlation (r) between organ and body weight in the different treatment groups.

| Treatment | Liver | Heart | Lung | Spleen | Kidney |
| --- | --- | --- | --- | --- | --- |
| PBS | 0.892 *** | 0.748 *** | 0.857 *** | 0.655 *** | 0.877 *** |
| 0.5 ng sFGFR3 | 0.883 ** | 0.777 ** | 0.731 * | 0.774 * | 0.777 ** |
| 5 ng sFGFR3 | 0.881 *** | 0.794 *** | 0.720 *** | 0.584 ** | 0.531 * |
| PBS | 0.941 *** | 0.943 *** | 0.886 ** | 0.726 ** | 0.848 *** |
| 0.5 ng sFGFR3 | 0.921 *** | 0.758 * | 0.709 ** | 0.650 * | 0.828 *** |
| 5 ng sFGFR3 | 0.957 *** | 0.983 *** | 0.885 *** | 0.883 *** | 0.850 *** |

Pearson or Spearman tests were used for statistical analysis of organ/body weights correlations in each treatment group; * p < 0.05;  p < 0.01; * p < 0.001. wt: wildtype mice; ach: Fgfr3$^{ach/+}$ mice.

TABLE S2

Blood biochemical parameters were not modified by FLAG-sFGFR3 treatment.

| | Treatment | Na (mmol/L) | K (mmol/L) | Cl (mmol/L) | LDH (UI/L) | Cholesterol (mmol/L) |
| --- | --- | --- | --- | --- | --- | --- |
| wt | PBS | 810.8 ± 80.8 | 9.26 ± 0.51 | 75.20 ± 3.81 | 1672 ± 124 | 0.99 ± 0.15 |
| | 5 ng sFGFR3 | 818.3 ± 69.4 | 8.75 ± 0.59 | 72.83 ± 1.14 | 2059 ± 478 | 0.90 ± 0.16 |
| ach | PBS | 709.7 ± 90.5 | 8.97 ± 0.98 | 81.79 ± 3.79 | 1675 ± 228 | 1.06 ± 0.11 |
| | 5 ng sFGFR3 | 706.2 ± 57.0 | 9.20 ± 0.77 | 76.33 ± 0.88 | 1738 ± 402 | 1.02 ± 0.08 |

| | Treatment | Creatinine (μmol/L) | Creatinine kinase (UI/L) | AST (UI/L) | ALT (UI/L) | Amylase (UI/L) | Total bilirubine (μmol/L) |
| --- | --- | --- | --- | --- | --- | --- | --- |
| wt | PBS | 9.00 ± 1.26 | 1389 ± 679 | 155.1 ± 27 | 65.5 ± 16.5 | 138.1 ± 4.7 | 22.8 ± 1.7 |
| | 5 ng sFGFR3 | 10.20 ± 0.95 | 655 ± 180 | 137.0 ± 24.6 | 42.3 ± 4.2 | 112.0 ± 8.0 | 20.8 ± 0.4 |

TABLE S2-continued

Blood biochemical parameters were not modified by FLAG-sFGFR3 treatment.

| | | | | | | | |
|---|---|---|---|---|---|---|---|
| ach | PBS | 9.18 ± 1.60 | 551 ± 127 | 140.1 ± 22.9 | 48.2 ± 14.6 | 129.8 ± 21.4 | 21.8 ± 1.1 |
| | 5 ng sFGFR3 | 12.33 ± 1.43 | 943 ± 261 | 196.4 ± 51.2 | 77.7 ± 14.5 | 192.0 ± 33.3 | 20.3 ± 0.6 |

To evaluate treatment toxicity, at time of sacrifice, plasma from the PBS and 5 ng FLAG-sFGFR3 groups were analyzed using a Beckman AU 2700 Analyzer. Overall health was evaluated by measurements of electrolytes ($Na^+$, $K^+$, $Cl^-$), lactate dehydrogenase (LDH) and cholesterol. Kidney function was assessed by creatinin and creatinin kinase (CK) assays. Liver and pancreas functions were assessed by aspartate aminotransferase (AST), alanine aminostransferase (ALT), total bilirubin (BLT) and amylase, respectively. Statistical comparisons were performed using a one way ANOVA. No statistical difference was found in any group, wt: wildtype mice; ach: $Fgfr3^{ach/+}$ mice.

TABLE S3

Blood counts were not modified by FLAG-sFGFR3 treatment.

| | Treatment | Hb (g/dL) | Ht (%) | WBC (K/µl) | RBC (K/µl) | PLT (K/µl) |
|---|---|---|---|---|---|---|
| wt | PBS | 8.11 ± 0.11 | 16.82 ± 1.72 | 4.31 ± 0.39 | 5.63 ± 0.02 | 471.1 ± 26.9 |
| | 5 ng sFGFR3 | 8.56 ± 0.06 | 23.21 ± 1.33 | 5.28 ± 0.54 | 5.81 ± 0.01 | 447.0 ± 32.2 |
| ach | PBS | 8.32 ± 0.26 | 22.5 ± 4.74 | 3.37 ± 0.49 | 5.47 ± 0.18 | 472.0 ± 112.8 |
| | 5 ng sFGFR3 | 8.25 ± 0.15 | 17.44 ± 1.12 | 5.86 ± 0.81 | 5.67 ± 0.04 | 620.0 ± 28.8 |

| | Treatment | NE (%) | LY (%) | MO (%) | EO (%) | BA (%) |
|---|---|---|---|---|---|---|
| wt | PBS | 30.76 ± 1.86 | 53.56 ± 2.49 | 7.52 ± 0.59 | 5.89 ± 0.44 | 2.27 ± 0.27 |
| | 5 ng sFGFR3 | 25.54 ± 2.37 | 56.90 ± 3.15 | 9.78 ± 0.67 | 5.75 ± 0.54 | 1.83 ± 0.24 |
| ach | PBS | 24.25 ± 6.08 | 60.02 ± 8.86 | 6.56 ± 1.48 | 6.59 ± 1.72 | 2.56 ± 0.59 |
| | 5 ng sFGFR3 | 29.25 ± 1.47 | 51.88 ± 2.39 | 10.16 ± 0.82 | 6.99 ± 1.20 | 1.85 ± 0.33 |

The effects of FLAG-sFGFR3 treatment on blood counts were evaluated on plasma samples at the time of sacrifice. Analysis included hemoglobin (Hb), hematocrit (Ht), white blood cells (WBC), red blood cells (RBC) and platelets (PLT) counts. The percentages of the different leukocyte populations were evaluated (NE: neutrophil; LY: lymphocyte, MO: monocyte, EO: eosinophil; BA: basophil). Statistical comparisons were performed using a one way ANOVA. No statistical difference was found in any group, wt: wildtype mice; ach: $Fgfr3^{ach/+}$ mice.

To evaluate unwanted side effects on fecundity, after the three week treatment, animals were weaned and were mated at age 8 weeks with wt FVB males or females from Charles River. As seen in Table 3, all treated animals were fertile and their offspring were of normal size with an approximate 50% wt/50% $Fgfr3^{ach/+}$ descendants. While $Fgfr3^{ach/+}$ females usually have a first litter slightly reduced in size compared to that of wt females, it is interesting to note that primiparous treated transgenic females had litters that were identical in size to wt primiparous females, confirming enlargement of their pelvis following treatment (Table 3).

TABLE 3

FLAG-sFGFR3 treatment did not affect fertility of the treated mice.

| | | Litter size | % of wt and ach at day 22 | Body weight (g) | Body length (mm) |
|---|---|---|---|---|---|
| Control genitors | ach ♂ × wt ♀ | 9.2 ± 0.9 | 74% wt, 26% ach | wt, 10.88 ± 1.62 | wt, 133.24 ± 6.11 |
| | wt ♂ × ach ♀ | 7.7 ± 0.7 *** | | ach, 8.66 ± 1.68 *** | ach, 117.25 ± 6.96 *** |
| sFGFR3 treated | treated ach ♂ × wt ♀ | 10.2 ± 1.9 | % wt, % ach | | |
| | treated wt ♂ × wt ♀ | 9.7 ± 0.9 | N/A | | |
| | wt ♂ × treated ach ♀ | 10.6 ± 1.5 | % wt, % ach | | |
| | wt ♂ × treated wt ♀ | 9.8 ± 1.9 | N/A | | |

Pups from two litters per group were weaned after the three week treatment. They were mated at age 8 weeks with wt animals from Charles River. The number of pups of the first litters was counted for each primiparous female. At age 22 days, animals were euthanized. Their body growth was evaluated as previously. A Student's t test was used to compare data to measurements of untreated wt animals generated from control genitors. *** $p < 0.001$ versus untreated wt. N/A: not applicable, wt: wildtype mice; ach: $Fgfr3^{ach/+}$ mice.

Altogether these experiments did not highlight any complications from the FLAG-sFGFR3 treatment itself neither on blood formulation, organ function and development nor fertility of the treated animals, suggesting that the use of a soluble form of FGFR3 may be a viable treatment approach for clinical applications.

DISCUSSION

The present study validates the proof of concept that a therapeutic strategy based on the use of a soluble form of FGFR3 can prevent abnormal bone growth in mice carrying the achondroplasia mutation. Treatment was administered twice a week by subcutaneous injections to the animals throughout the growth period. Following this three week treatment period, ensuing endochondral bone growth led to normal, harmonious stature. Importantly, these effects were dose-dependent; the dose of 0.5 ng FLAG-sFGFR3 was sufficient to induce body weight and length that were identical to that of untreated wt mice and at the dose of 5 ng, treated dwarf mice were even heavier and had longer long bones than untreated wt animals. Foremost, the present results emphasize the notion that the achondroplasia mutation requires ligand binding to be activated. Indeed, it has been demonstrated that in the case of the G380R mutation, FGFR3 activation is ligand-dependant (12), but there is still no clear consensus in the literature (29-31), suggesting not one but multiple mechanisms leading to prolonged intracellular signaling.

While it was essential that long bone growth be restored for the treatment to be effective, it was critical to also significantly impact the onset of complications, due to skeletal deformities. For the inventors, this is indispensable if one wants to develop a treatment for the clinic. Restoration of vertebra maturation and normal closure of cranial synchondroses in treated Fgfr3$^{ach/+}$ mice had numerous effects on these animals. The first consequence was the reduced mortality among the transgenic population. As stated in the result section, autopsy revealed respiratory failures in the majority of the cases. Based on the anatomical characteristics of the skull and vertebrae of the dwarf mice, the inventors believe that these were consequent to brainstem compression, similar to what can be observed in achondroplasia patients.

A second outcome of treatment effect was a shift in the penetrance of the phenotype. While measurements could appear as though treatment effects were not totally dose-dependent and more importantly not as effective as could be expected based on body weights, the inventors believe that at the highest dose, treatment saved the smallest Fgfr3$^{ach/+}$ mice from brainstem compression and respiratory failure. Untreated, these animals would not have survived past week 1 or 2. In this treatment group, the inventors hypothesize that these animals are those that remain very small even though they have less severe complications.

Despite the increasing number of reports studying the mechanisms underlying achondroplasia and related skeletal dysplasia, only three studies have been published showing therapeutic strategies effectively tested in mice with chondrodysplasia. Xie et al. recently published a report that intermittent PTH treatment partially rescues bone growth in mice with achondroplasia (32). In their study, PTH was administered subcutaneously at the dose of 100 µg/kg body weight per day for 4 weeks after birth. Although the mechanism by which PTH affects FGFR3 intracellular signaling is not clearly established, bone growth was partially rescued in treated transgenic mice; PTH treated transgenic mice were still smaller than their wt littermates. In this study, only very little information was mentioned related to achondroplasia complications, except for the partial rescue of cranial synchondrose. The lethal phenotype of TDII mice was also rescued with chronic PTH treatment of pregnant females. Another potential therapeutic antagonist of FGFR3 signaling is the C-natriuretic peptide (CNF) (33). In this paper, the authors treated transgenic mice with achondroplasia by continuous intravenous infusion of synthetic CNP for 3 weeks starting at age 4 week. It is believe that CNP increases the width of the growth plate accelerating growth plate activity. The major obstacle for use in human is the very short half-life of CNP, estimated to be 2.6 min in plasma (34).

A study has been very recently published describing the use of a new FGFR3-binding peptide that rescues the lethal phenotype and partially restores the structural distortion of growth plates in TDII mice, observed on 12 pups (19). In this study, effects on MAPK signaling and bone growth correction were only partial and daily administration was required probably due to the short half-life of the peptide. Here, the effects of sFGFR3 were of higher magnitude, with complete restoration of normal stature. The inventors believe that the half-life of the soluble form of FGFR3 containing IgG like domains is significantly prolonged. Indeed, only 6 injections (between birth and weaning) were necessary to completely restore bone growth in the 86 treated Fgfr3$^{ach/+}$ mice. They can imagine that only a few injections would be necessary to treat achondroplasia children as out-patients, starting during the first year until puberty. This would substantially impact occurrence of injection side effects, typically found with daily injection regimens. The use of a soluble recombinant protein also allows for rapid termination during treatment if safety issues are raised and at puberty when bone growth ceases. If necessary, it is also possible to alternate between treatment and resting periods. By preventing the complications, sFGFR3 treatment would avoid the necessity of surgical interventions and also reduce any stress due to hospitalization. Furthermore, our study did not reveal any toxicological effect on blood or fertility and offspring of treated animals. Current studies are ongoing to evaluate if the three week sFGFR3 treatment had an effect on the long-term health of the treated mice. As of today, treated mice are 6 month old and no apparent side effects are visible and blood tests are normal.

In conclusion, the present study demonstrates the viability of targeting FGFR3 in the extracellular compartment as an effective treatment to restore growth plate maturation and induce normal bone growth in achondroplasia. The absence of unwanted side effects validates its use as a promising therapy for this and related chondrodysplasia caused by activating mutation in FGF receptors. Furthermore, in the present study, the inventors also report a positive effect of sFGFR3 treatment on the growth of wt animals. This is of importance suggesting its possible interest for the treatment of idiopathic growth retardations, or to prevent severe complications in other rare diseases such as hypophosphatasia.

REFERENCES

Throughout this application, various references describe the state of the art to which this invention pertains. The disclosures of these references are hereby incorporated by reference into the present disclosure.

1. D. M. Ornitz, FGF signaling in the developing endochondral skeleton. Cytokine Growth Factor Rev 16, 205 (April, 2005).

2. M. L. Martinez-Frias, C. A. de Frutos, E. Bermejo, M. A. Nieto, Review of the recently defined molecular mechanisms underlying thanatophoric dysplasia and their potential therapeutic implications for achondroplasia. Am J Med Genet A 152A, 245 (January, 2010).

3. W. A. Horton, G. P. Lunstrum, Fibroblast growth factor receptor 3 mutations in achondroplasia and related forms of dwarfism. Rev Endocr Metab Disord 3, 381 (December, 2002).

4. M. J. Wright, M. D. Irving, Clinical management of achondroplasia. Arch Dis Child 97, 129 (February, 2012).

5. W. A. Horton, J. G. Hall, J. T. Hecht, Achondroplasia. Lancet 370, 162 (Jul. 14, 2007).

6. E. D. Shirley, M. C. Ain, Achondroplasia: manifestations and treatment. J Am Acad Orthop Surg 17, 231 (April, 2009).

7. P. Richette, T. Bardin, C. Stheneur, Achondroplasia: from genotype to phenotype. Joint Bone Spine 75, 125 (March, 2008).

8. F. Rousseau et al., Mutations in the gene encoding fibroblast growth factor receptor-3 in achondroplasia. Nature 371, 252 (Sep. 15, 1994).

9. G. A. Belius et al., Achondroplasia is defined by recurrent G380R mutations of FGFR3. Am J Hum Genet 56, 368 (February, 1995).

10. R. Shiang et al., Mutations in the transmembrane domain of FGFR3 cause the most common genetic form of dwarfism, achondroplasia. Cell 78, 335 (Jul. 29, 1994).

11. F. Rousseau et al., Mutations of the fibroblast growth factor receptor-3 gene in achondroplasia. Horm Res 45, 108 (1996).

12. E. Monsonego-Oman, R. Adar, T. Feferman, O. Segev, A. Yayon, The transmembrane mutation G380R in fibroblast growth factor receptor 3 uncouples ligand-mediated receptor activation from down-regulation. Mol Cell Biol 20, 516 (January, 2000).

13. D. Harada el al., Sustained phosphorylation of mutated FGFR3 is a crucial feature of genetic dwarfism and induces apoptosis in the ATDC5 chondrogenic cell line via PLC gamma-activated STAT1. Bone 41, 273 (August, 2007).

14. E. Monsonego-Oman, R. Adar, E. Rom, A. Yayon, FGF receptors ubiquitylation: dependence on tyrosine kinase activity and role in downregulation. FEBS Lett 528, 83 (Sep. 25, 2002).

15. M. K. Webster, D. J. Donoghue, Constitutive activation of fibroblast growth factor receptor 3 by the transmembrane domain point mutation found in achondroplasia. Embo J 15, 520 (Feb. 1, 1996).

16. M. B. Lacderich, W. A. Horton, FGFR3 targeting strategies for achondroplasia. Expert Rev Mol Med 14, el 1 (2012).

17. C. Deng, A. Wynshaw-Boris, F. Zhou, A. Kuo, P. Leder, Fibroblast growth factor receptor 3 is a negative regulator of bone growth. Cell 84, 911 (Mar. 22, 1996).

18. Z. Vajo. C. A. Francomano, D. J. Wilkin, The molecular and genetic basis of fibroblast growth factor receptor 3 disorders: the achondroplasia family of skeletal dysplasias, Muenke craniosynostosis, and Crouzon syndrome with acanthosis nigricans. Endocr Rev 21, 23 (February, 2000).

19. M. Jin et al., A novel FGFR3-binding peptide inhibits FGFR3 signaling and reverses the lethal phenotype of mice mimicking human thanatophoric dysplasia. Hum Mol Genet, (Oct. 9, 2012).

20. S. Garofalo et al., Skeletal dysplasia and defective chondrocyte differentiation by targeted overexpression of fibroblast growth factor 9 in transgenic mice. J Bone Miner Res 14, 1909 (November, 1999).

21. D. Davidson et al., Fibroblast growth factor (FGF) 18 signals through FGF receptor 3 to promote chondrogenesis. J Biol Chem 280, 20509 (May 27, 2005).

22. M. C. Naski, J. S. Colvin, J. D. Coffin, D. M. Ornitz, Repression of hedgehog signaling and BMP4 expression in growth plate cartilage by fibroblast growth factor receptor 3. Development 125, 4977 (December, 1998).

23. T. D. Papakostas et al., Development of an efficiently cleaved, bioactive, highly pure FLAG-tagged recombinant human Mullerian Inhibiting Substance. Protein Expr Purif 70, 32 (March, 2010).

24. K. Terpe, Overview of tag protein fusions: from molecular and biochemical fundamentals to commercial systems. Appl Microbiol Biotechnol 60, 523 (January, 2003).

25. J. P. Louboutin, B. A. Reyes, L. Agrawai, E. Van Bockstaele, D. S. Strayer, Strategies for CNS-directed gene delivery: in vivo gene transfer to the brain using SV40-derived vectors. Gene Ther 14, 939 (June, 2007).

26. L. R. Rodino-Klapac et al., Persistent expression of FLAG-tagged micro dystrophin in nonhuman primates following intramuscular and vascular delivery. Mol Ther 18, 109 (January, 2010).

27. F. M. Altaf, T. M. Hering, N. H. Kazmi, J. U. Yoo, B. Johnstone, Ascorbate-enhanced chondrogenesis of ATDC5 cells. Eur Cell Mater 12, 64 (2006).

28. N. Laws, A. Hoey, Progression of kyphosis in mdx mice. J Appl Physiol 97, 1970 (November, 2004).

29. J. Placone, K. Hristova, Direct Assessment of the Effect of the Gly380Arg Achondroplasia Mutation on FGFR3 Dimerization Using Quantitative Imaging FRET. PLoS One 7, e46678 (2012).

30. L. He, W. Horton, K. Hristova, Physical basis behind achondroplasia, the most common form of human dwarfism. J Biol Chem 285, 30103 (Sep. 24, 2010).

31. L. He, N. Shobnam, W. C. Wimley, K. Hristova, FGFR3 heterodimerization in achondroplasia, the most common form of human dwarfism. J Biol Chem 286, 13272 (Apr. 15, 2011).

32. Y. Xie et al., Intermittent PTH (1-34) injection rescues the retarded skeletal development and postnatal lethality of mice mimicking human achondroplasia and thanatophoric dysplasia. Hum Mol Genet 21, 3941 (Sep. 15, 2012).

33. A. Yasoda et al., Systemic administration of C-type natriuretic peptide as a novel therapeutic strategy for skeletal dysplasias. Endocrinology 150, 3138 (July, 2009).

34. P. J. Hunt, A. M. Richards, E. A. Espiner, M. G. Nicholls, T. G. Yandle, Bioactivity and metabolism of C-type natriuretic peptide in normal man. J Clin Endocrinol Metab 78, 1428 (June, 1994).

35. M. Terada et al., Fibroblast growth factor receptor 3 lacking the Ig IIIb and transmembrane domains secreted from human squamous cell carcinoma DJM-1 binds to FGFs. Mol Cell Biol Res Commun 4, 365 (November, 2001).

36. A. Bertola et al., Hepatocyte growth factor induces glucose uptake in 3T3-L1 adipocytes through A Gab1/phosphatidylinositol 3-kinase/Glut4 pathway. J Biol Chem 282, 10325 (April, 2007).

The invention claimed is:

1. A method for treating a FGFR3-related skeletal growth retardation disorder in a subject in need thereof, the method comprising administering to the subject a soluble Fibroblast Growth Factor Receptor 3 (sFGFR3) polypeptide comprising amino acids 1-375 of a naturally-occurring human FGFR3 adjacent to an intracellular domain of the naturally-occurring human FGFR3, and lacking a transmembrane domain of the naturally-occurring human FGFR3, wherein the naturally-occurring human FGFR3 comprises the amino acid sequence as set forth in SEQ ID NO: 3.

2. The method of claim 1, wherein the FGFR3-related skeletal growth retardation disorder is thanatophoric dysplasia type I (TDI), thanatophoric dysplasia type II (TDII), severe achondroplasia with developmental delay and acanthosis nigricans (SADDAN), hypochondroplasia, achondroplasia, Muenke syndrome, or Crouzon syndrome with acanthosis nigricans.

3. The method of claim 2, wherein the FGFR3-related skeletal growth retardation disorder is achondroplasia.

4. The method of claim 2, wherein the FGFR3-related skeletal growth retardation disorder is hypochondroplasia.

5. The method of claim 1, wherein the subject is a human.

6. The method of claim 1, wherein the FGFR3-related skeletal growth retardation disorder is caused by expression in the subject of an FGFR3 variant that exhibits ligand-dependent overactivation.

7. The method of claim 6, wherein the FGFR3 variant comprises an amino acid substitution of a glycine residue at position 380 of wild-type FGFR3 with an arginine residue (G380R).

8. The method of claim 1, wherein the subject is administered 0.0002 mg/kg/day to 20 mg/kg/day of the sFGFR3 polypeptide.

9. The method of claim 1, wherein the subject is administered 0.001 mg/kg/day to 7 mg/kg/day of the sFGFR3 polypeptide.

10. The method of claim 1, wherein the sFGFR3 polypeptide is administered subcutaneously.

11. The method of claim 1, wherein the sFGFR3 polypeptide is administered intravenously.

\* \* \* \* \*